(12) United States Patent
Whitmore, III et al.

(10) Patent No.: US 7,395,563 B2
(45) Date of Patent: Jul. 8, 2008

(54) SUPPORT SYSTEM FOR USE WHEN PERFORMING MEDICAL IMAGING OF A PATIENT

(75) Inventors: Willet F. Whitmore, III, Longboat Key, FL (US); Roger F. Wilson, Sarasota, FL (US); Gary M. Onik, Orlando, FL (US); Winston E. Barzell, Sarasota, FL (US); Stephen E. Brauner, Bradenton, FL (US)

(73) Assignee: CIVCO Medical Instruments Co., Inc., Kalona, IA (US)

( * ) Notice: Subject to any disclaimer, the term of this patent is extended or adjusted under 35 U.S.C. 154(b) by 0 days.

(21) Appl. No.: 11/095,586

(22) Filed: Apr. 1, 2005

(65) Prior Publication Data
US 2006/0016006 A1  Jan. 26, 2006

Related U.S. Application Data

(60) Provisional application No. 60/559,414, filed on Apr. 2, 2004, provisional application No. 60/575,792, filed on May 28, 2004, provisional application No. 60/614,593, filed on Oct. 1, 2004.

(51) Int. Cl.
*A61B 6/04* (2006.01)
*A61B 17/00* (2006.01)
*A61G 13/10* (2006.01)

(52) U.S. Cl. .................. 5/601; 5/600; 5/621; 378/209; 248/276.1

(58) Field of Classification Search .............. 5/601, 5/600, 621–625, 658, 663, 503.1, 507.1; 378/209, 204, 208, 20; 248/276.1, 279.1, 248/160; 600/228, 229
See application file for complete search history.

(56) References Cited

U.S. PATENT DOCUMENTS 3,858,578 A  1/1975  Milo .......................... 128/20

(Continued)

FOREIGN PATENT DOCUMENTS

GB  2 094 590 A  9/1982

(Continued)

OTHER PUBLICATIONS

Christopher Nimsky et al., "Intraoperative Magnetic Resonance Imaging Combined with Neuronavigation: A New Concept," *Neurosurgery*, vol. 48, No. 5, May 2001, pp. 1082-1091.

(Continued)

*Primary Examiner*—Robert G Santos
(74) *Attorney, Agent, or Firm*—Steptoe & Johnson LLP

(57) ABSTRACT

A system is provided for supporting a patient during computed axial tomography imaging. The system includes a movable platform formed of a radiolucent material, a discrete attachment region in the platform, and a curvilinear articulating arm coupled to the platform at the discrete attachment region. A method for supporting a patient during a plurality of procedures also is provided. The method includes: disposing the patient on a movable platform formed of a radiolucent material; positioning a device with respect to the patient, the device being disposed on a curvilinear articulating arm coupled to the platform; placing the platform, positioned device, and patient in a computed axial tomography imaging system and performing an imaging procedure.

12 Claims, 28 Drawing Sheets

U.S. PATENT DOCUMENTS

| | | | | |
|---|---|---|---|---|
| 4,465,069 | A | 8/1984 | Barbier et al. | 128/303 B |
| 4,473,912 | A | 10/1984 | Scheidel et al. | 5/82 R |
| 4,566,445 | A | 1/1986 | Jelsma et al. | 128/70 |
| 4,583,538 | A | 4/1986 | Onik et al. | 128/303 B |
| 4,592,352 | A | 6/1986 | Patil | 128/303 B |
| 4,686,997 | A | 8/1987 | Oloff et al. | 128/653 |
| 4,733,661 | A | 3/1988 | Palestrant | 128/303 B |
| 4,791,934 | A | 12/1988 | Brunnett | 128/653 |
| 4,854,305 | A | 8/1989 | Bremer | 128/75 |
| 5,280,427 | A | 1/1994 | Magnusson et al. | 364/413.01 |
| 5,410,769 | A | 5/1995 | Waterman | 5/632 |
| 5,499,415 | A | 3/1996 | McKenna | 5/601 |
| 5,513,827 | A * | 5/1996 | Michelson | 248/279.1 |
| 5,537,454 | A | 7/1996 | Korver, II | 378/65 |
| 5,771,513 | A * | 6/1998 | Kirchgeorg et al. | 5/625 |
| 5,842,987 | A | 12/1998 | Sahadevan | 600/407 |
| 5,865,780 | A | 2/1999 | Tuite | 602/32 |
| 5,876,325 | A * | 3/1999 | Mizuno et al. | 600/102 |
| 6,003,174 | A | 12/1999 | Kantrowitz et al. | 5/601 |
| 6,161,237 | A | 12/2000 | Tang et al. | 5/621 |
| 6,199,233 | B1 | 3/2001 | Kantrowitz et al. | 5/601 |
| 6,266,831 | B1 | 7/2001 | Heimbrock | 5/601 |
| 6,322,251 | B1 | 11/2001 | Ballhaus et al. | 378/209 |
| 6,378,149 | B1 * | 4/2002 | Sanders et al. | 5/624 |
| 6,499,158 | B1 * | 12/2002 | Easterling | 5/600 |
| 6,584,630 | B1 | 7/2003 | Dinkler | 5/622 |
| 6,598,275 | B1 * | 7/2003 | Kolody et al. | 24/455 |
| 6,671,904 | B2 * | 1/2004 | Easterling | 5/601 |
| 6,681,423 | B2 | 1/2004 | Zachrisson | 5/610 |
| 6,718,571 | B2 | 4/2004 | Bartels | 5/81.1 R |
| 6,730,020 | B2 | 5/2004 | Peng et al. | 600/201 |
| 6,731,970 | B2 | 5/2004 | Schlossbauer et al. | 600/428 |
| 6,772,461 | B2 | 8/2004 | Gaspar | 5/632 |
| 6,782,571 | B1 | 8/2004 | Josephson et al. | 5/601 |
| 6,912,959 | B2 * | 7/2005 | Kolody et al. | 108/28 |
| 7,020,917 | B1 * | 4/2006 | Kolody et al. | 5/621 |
| 7,159,832 | B2 * | 1/2007 | Easterling | 248/316.6 |
| 2002/0032927 | A1 | 3/2002 | Dinkler | 5/601 |
| 2004/0092810 | A1 | 5/2004 | Daum et al. | 600/411 |
| 2004/0143177 | A1 | 7/2004 | Falbo, Sr. et al. | 600/407 |
| 2004/0176751 | A1 * | 9/2004 | Weitzner et al. | 606/1 |
| 2006/0016006 | A1 * | 1/2006 | Whitmore et al. | 5/601 |

FOREIGN PATENT DOCUMENTS

WO     WO 99/11176     3/1999

OTHER PUBLICATIONS

S. H. Heywang-Köbrunner et al., "MR-Guided Percutaneous Vacuum Assisted Biopsy of Enhancing Breast Lesions," *electromedica* 67 (1999) No. 2, pp. 37-45.

Th. J. Vogl et al., "MR-Guided Interventions with a DSA-MRI Hybrid System," *electromedica* 68 (2000) No. 2, pp. 116-121.

G. J. Rubino et al., "Interventional Magnetic Resonance Imaging Guided Neurosurgery—The UCLA Experience with the First 100 Cases," *electromedica* 68—*neuro* 2000, pp. 37-46.

Daniel F. Kacher et al., "Design and Implementation of Surgical Instruments, Devices, and Receiver Coils for Intraoperative MRI-Guided Neurosurgical and Neuro Ablative Procedures," *Automedica*, 2001, 00:1-45, SPL Technical Report #205, Surgical Planning Laboratory (SPL), Brigham and Women's Hospital, Boston, MA, posted Mar. 2001, http://splweb.bwh.harvard.edu:8000/pages/current_projects.html.

"Flexbar Scope Holder," Thompson Surgical Instruments, Inc., brochure, 2 pages.

"IPPS: The Basics," MEDTEC, 2 pages, http://www.medtec.com/products/immobilization/ipps/overview.htm.

"Computed Tomography. Interventional CT," Koninklijke Philips Electronics N.V., 1 page printed Jul. 12, 2004, 2 pages printed Oct. 7, 2005, http://www.medical.philips.com/main/products/ct/products/interventional/.

"Computed Tomography. Multislice CT. Standard Accessories," Koninklijke Philips Electronics N.V., 2 pages printed Jul. 12, 2004, 4 pages printed Oct. 7, 2005, http://www.medical.philips.com/main/products/ct/products/interventional/.

"Radiation Oncology Systems. ACQSIM CT Simulation," Koninklijke Philips Electronics N.V., 1 page printed Jul. 12, 2004, 2 pages printed Oct. 7, 2005, http://www.medical.philips.com/main/products/ros/products/acqsim_ct/.

\* cited by examiner

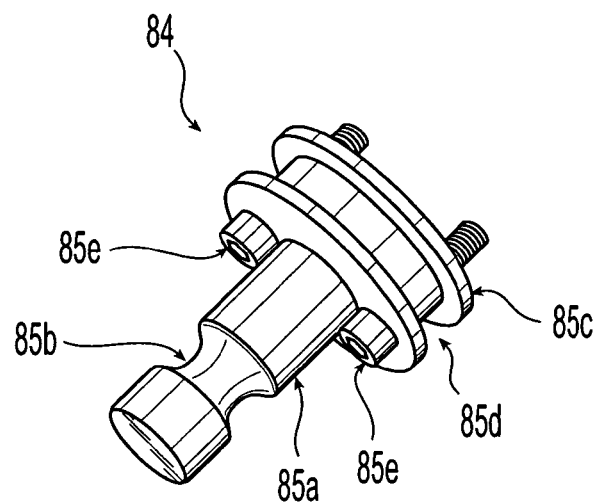
FIG. 5H
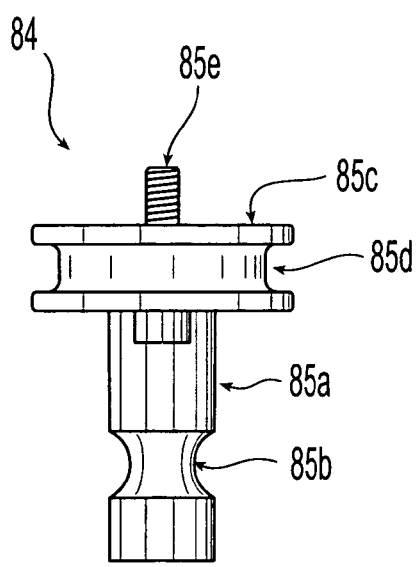
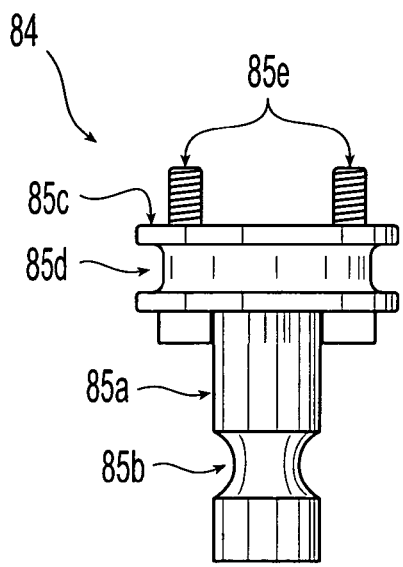
FIG. 5I          FIG. 5J

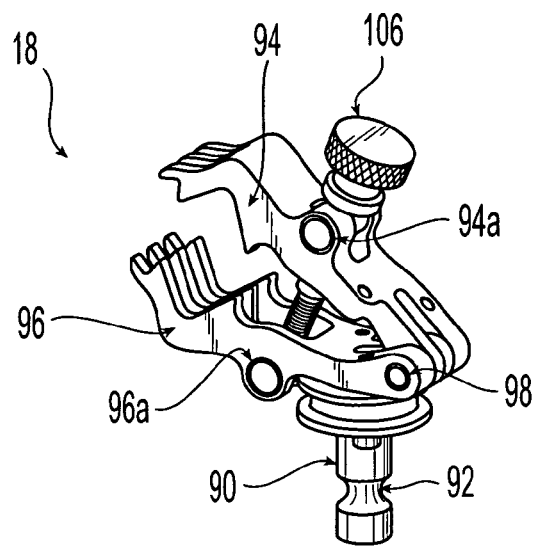
FIG. 6A
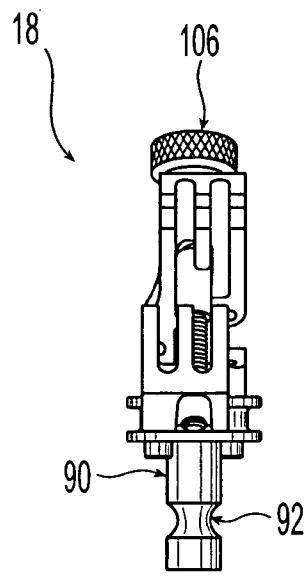 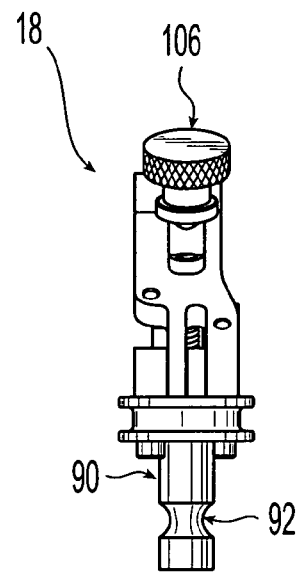
FIG. 6B    FIG. 6C

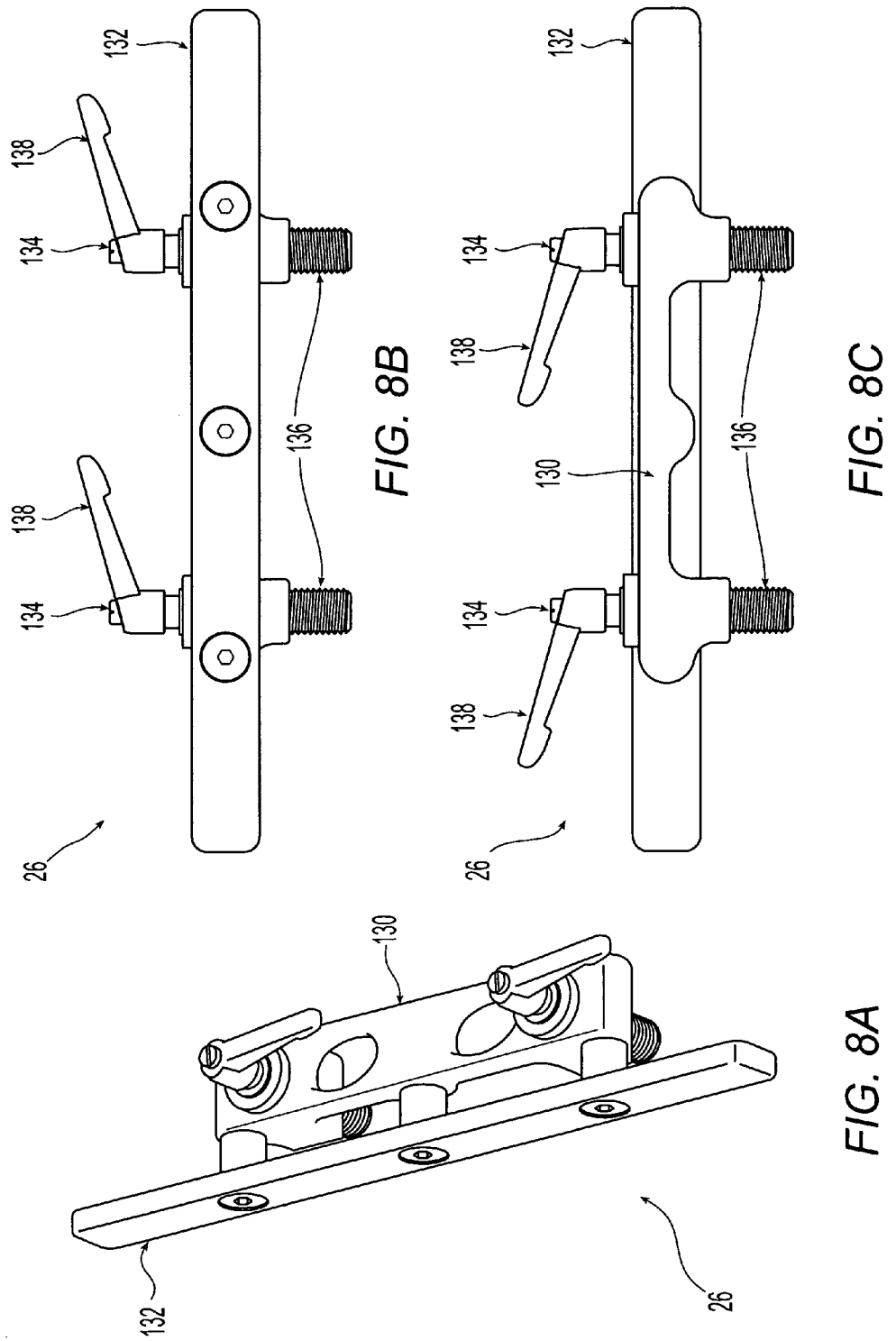

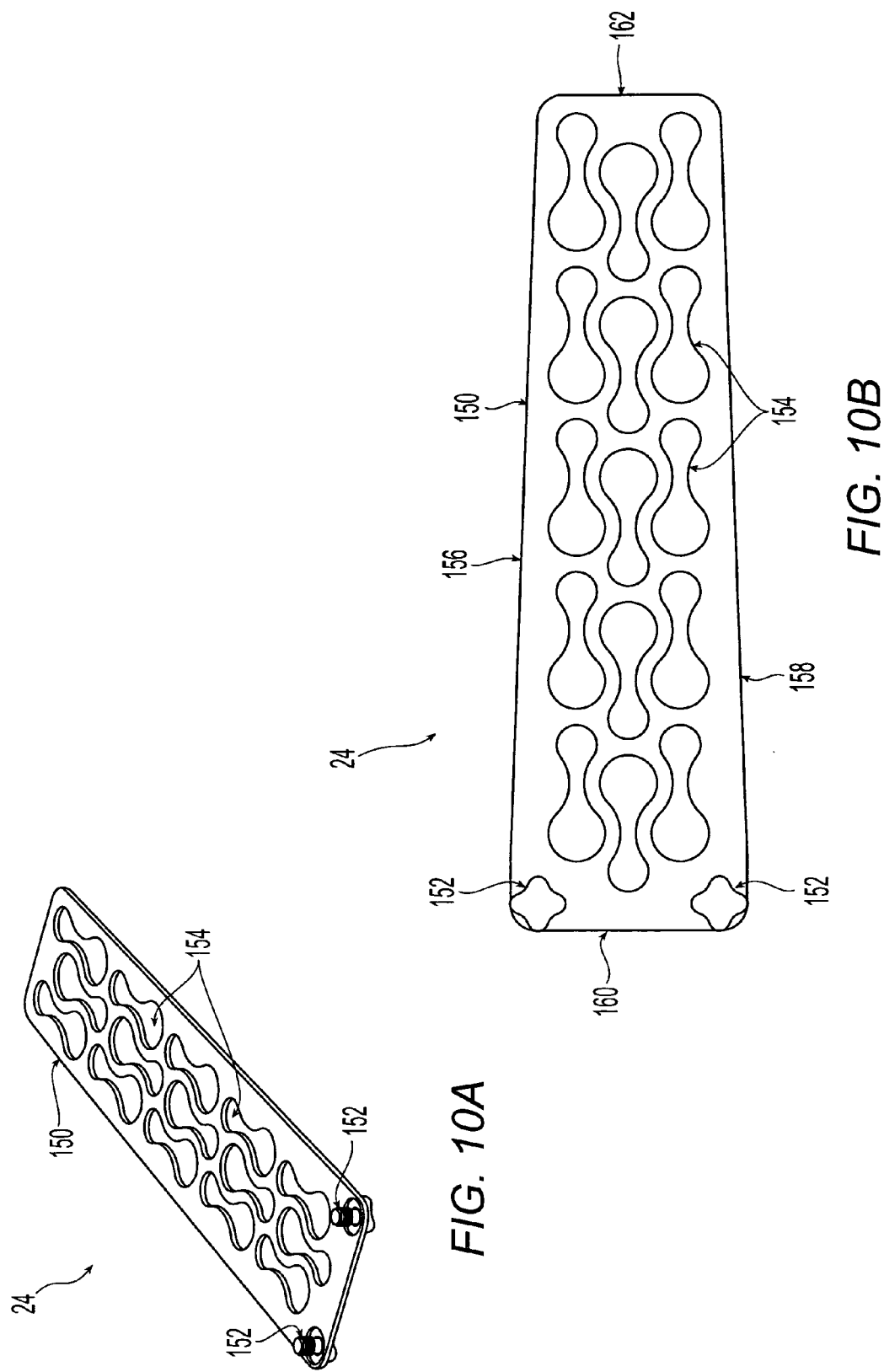

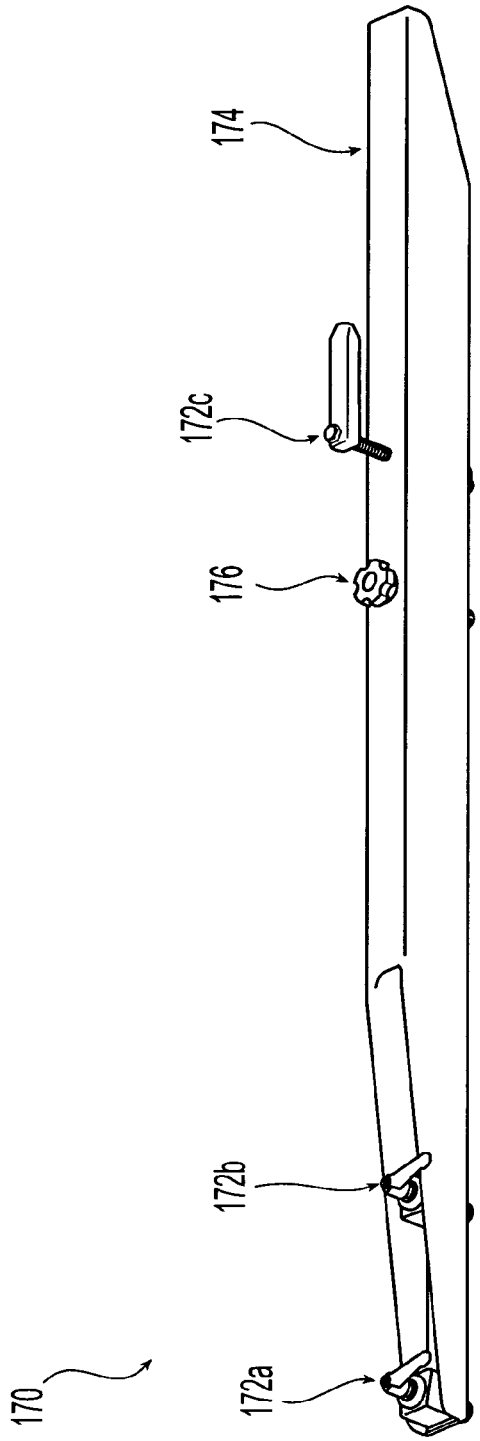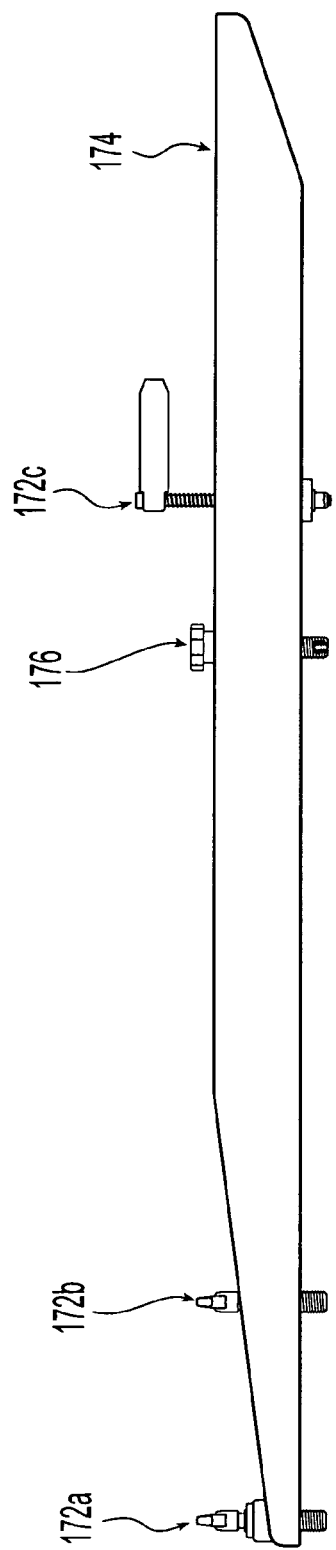
FIG. 11A
FIG. 11B

SUPPORT SYSTEM FOR USE WHEN PERFORMING MEDICAL IMAGING OF A PATIENT

CROSS-REFERENCE TO RELATED APPLICATIONS

The benefits of Provisional Application No. 60/559,414 filed Apr. 2, 2004, Provisional Application No. 60/575,792 filed May 28, 2004, and Provisional Application No. 60/614,593 filed Oct. 1, 2004 are claimed under 35 U.S.C. § 119(e), and the entire contents of these applications are expressly incorporated herein by reference thereto.

FIELD OF THE INVENTION

The invention relates to a support system for use when performing medical imaging of a patient. In particular, the invention relates to a patient support tray adapted to use in a variety of medical environments.

BACKGROUND OF THE INVENTION

Work-flows of patients from arrival at medical care facilities through post-operative recovery typically require a patient to be transferred among multiple supports on which the patient is transported and/or stabilized. For example, upon arrival at a hospital via an ambulance, a patient initially may be moved on a stretcher into the hospital. The patient then may be transferred to a hospital gurney and moved to an imaging room for assessment. In the imaging room, the patient may be transferred to an imaging table such as an x-ray table, and then returned to the gurney. Subsequently, the patient may be transferred to a patient bed while recovering or awaiting further evaluation, and/or the patient may be brought to an operating room (OR) and transferred to an operating table. Such extensive repositioning of the patient has numerous disadvantages, including a reduced ability to generally immobilize the patient, increased personnel requirements due to assisting or lifting the patient from one support to another, and even the potential for injuries to hospital personnel because of the lifting. Nevertheless, a standard patient support suitable for use in multiple hospital environments thus far has not been introduced because of the diverse design requirements that must be met for widespread application.

Patient supports used in ambulance settings, for example, must meet different standards from patient supports used in conjunction with imaging technologies. When transporting a patient in an ambulance, the patient must be immobilized so that further injury does not occur during transport. Some instrumentation may need to be supported, such as an intravenous (IV) bag, and this instrumentation may be coupled to the patient gurney. In contrast, in the imaging setting, many materials may not be present with the patient due to interference with the operation of the imaging equipment. Thus, the patient typically is supported on a tabletop or tray that is generally free of additional medical equipment. And, in some instances, several patient settings are needed at the same time, for example imaging while a patient undergoes surgery. It is clear that a patient support with generic use across many of the patient settings would be desirable. An explanation of the particular requirements of some of these settings thus is next introduced.

Various diagnostic imaging technologies are known for visualization of internal organs and structures. Computed axial tomography (CT), for example, is an x-ray scanning technique for producing cross-sectional images, while magnetic resonance imaging (MR) is a radiation-free technique that uses a strong magnet and radiofrequency waves to produce images in desired "slice planes." During CT and MR procedures in the clinical or operating room setting, a patient is placed on a movable support that translates within a housing. Traditional CT and MR equipment includes a ring-type gantry, and the patient is moved within the gantry so that images may be acquired of the anatomical region of interest. CT is known to be particularly useful for volumetric imaging but also suffers from poor soft tissue contrast, while MRI offers multi-planar imaging with superior soft tissue contrast.

The use of CT and MR for intraoperative imaging and interventional radiology (e.g., performing minimally invasive, targeted treatments using imaging for guidance) previously has been limited because of the substantial challenges posed by the geometry and overall size of the imaging equipment. The donut-shaped, ring-type gantries of traditional CT and MR equipment, for example, are not easily accommodated in operating rooms, and can cause or suffer from various deleterious effects due to interactions with other equipment. However, advances in CT and MR equipment are permitting more widespread application in intraoperative and interventional applications.

Until recently, only simple procedures such as biopsy or aspiration of fluid were performed in these scanners, and the need for additional capabilities in the support or table was limited. However, dramatic improvements in the image resolution and the speed of image acquisition of modern CT and MR scanners, the development of software and tracking technology for instrument guidance that can correlate with the images, and the development of software that permits the integration of multiple imaging modalities has greatly stimulated the use of these scanners in therapeutic procedures where image guidance can improve safety and efficacy. Some of the new minimally invasive ablative therapies require high precision placement of the delivery probes, and the monitoring and documentation achieved with concurrent CT or MR imaging is essential. Also, some newly developed surgeries simply cannot be done without concurrent CT or MR image guidance.

In such imaging procedures, the movable imaging support typically is provided on a base or carriage that receives the support at a desired height. For example, as disclosed in U.S. Pat. No. 6,161,237 to Tang et al., assigned to Med-Tec, Inc., a table base or carriage is provided with a tabletop that is mounted for longitudinal movement upon side rails attached to opposite sides of the carriage.

Imaging supports for movement on a carriage may be generally featureless, and simply may be sized to accommodate patients of a given height, weight, and girth. The supports may form patient couches when, for example, radiotranslucent cushions are placed along the supports and attached for example using Velcro®. Such cushions may enhance patient comfort and also may be readily conformable to a patient's anatomical contours so that patient movement is minimized. Typically, such a scanning tray is formed of a polymer or composite and has a smooth, generally flush and featureless surface. The tray may be cantilevered and slides into the gantry, with movement of the tray controlled by imaging software so that elevational and longitudinal positions may be set as needed.

A single imaging support also may be used with multiple imaging systems, as disclosed for example in U.S. Pat. No. 6,782,571 to Josephson et al., assigned to GE Medical Systems. As described in the patent, mobile patient transport is provided, allowing for patient setup outside of imaging bays. A patient may be quickly transferred between imaging systems without lifting the patient, and a dual end docking of the patient transport allows in line motion of the patient between systems, thus minimizing patient disruption.

The surrounding geometry of the imaging equipment, along with the requisite patient translation during scanning, presents a challenge when performing invasive procedures that require or are benefited by having equipment that ideally should remain in a fixed relationship to the immobilized patient. For example, a typical practice is to hold medical instruments manually, rely on gravity, tissue structure and friction, and to improvise props using towels or other padding. However, as procedures are becoming more complex and, in particular, as CT and MR imaging equipment are moved into the operating room environment, there is a need for new approaches. Because of the needs of medical personnel conducting intraoperative and interventional procedures, new patient supports and associated components, and new instrument positioning and holding devices and methods are desired to address these needs.

A variety of modifications have been proposed or implemented for intraoperative procedures, particularly involving MRI. For example, it has been reported that patient tables may be modified to allow efficient transition between the MR scanner and the surgical pedestal, the tables may be tilted (Trendelenburg, reverse Trendelenburg), rotated/pivoted, elevated and/or lowered, and the patient can be translated past the outer edge of the scanner into the fringe field when scanning is not required. In addition, rigid skull clamps have been fixed to such a table. See, e.g., Daniel F. Kacher et al., "Design and Implementation of Surgical Instruments, Devices, and Receiver Coils for Intraoperative MRI-Guided Neurosurgical and Neuro Ablative Procedures," *Automedica* (2001); G. J. Rubino et al., "Interventional Magnetic Resonance Imaging Guided Neurosurgery—The UCLA Experience with the First 100 Cases," Electromedica 68—neuro 2000, pp. 37-46.

Also known is a hybrid system in which an MRI scanner is connected to a digital subtraction angiography (DSA) unit by a 2.8 meter connecting table for patient repositioning, the connecting table being disposed between a standard removable MR table and the angiographic unit table. The imaging units are installed in adjacent rooms that may be separated by a shielding door, thereby allowing patient access to either system. The special table and environment of the combined imaging suite, however, required a custom-built clinical setup. See Th. J. Vogl, "MR-Guided Interventions with a DSA-MRI Hybrid System," *Electromedica* 68 (2), pp. 116-121 (2000).

Some materials suitable for use in patient supports and associated components for use in the operating environment are unsuitable for use in the imaging environment. Because a strong magnetic field is created during MRI, ferromagnetic metal objects (and many other magnetic objects) must be kept out of the proximity of the machine. Such metal objects may cause poor image resolution and result in image artifacts that can mask or be misinterpreted as pathology. Concomitantly, metal objects present a safety hazard to the patient due to their attraction to the magnetic source (e.g., becoming projectiles due to their attraction by the magnet to the vicinity of the scanner table). Thus, high carbon steel alloys and pure iron must be avoided. Carbon fiber, a radiolucent material that is essentially transparent to x-rays, often is used in the CT setting but not generally accepted for use with an MRI scanner.

Thus, even the design of a patient support for use in just two different settings—such as the OR and the MR imaging environment—must meet a variety of requirements particular to each setting.

Along with the need for a new support for a patient, a variety of additional new components and methods may be desired by the technician, physician or surgeon. For example, one possible advance that may be achieved by application of such new CT and MR equipment is respiratory gating.

It is well known that the chest and abdominal organs can move several inches during respiration. One resulting problem is that this anatomical motion can adversely affect data acquisition, causing so-called ghost, or motion artifacts and thus adversely affect image quality. This problem is traditionally managed by asking patients to hold their breath, or by halting respiration if it is controlled mechanically, during the acquisition of images. A second problem arises when interventional procedures are done because of the inability of a patient to precisely repeat a given breath. This repetition is essential for accurate image correlation with a patient's anatomy when he or she is moved out of the scanner. Thus, for safety and efficacy, it is desirable to employ some method for monitoring and recording respiratory position at the time of acquisition of the CT or MR targeting image(s) that can be used to repeat that same anatomic position at the time of instrument placement. Such an exercise defines respiratory gating. Techniques have been developed for synchronizing cardiac and vascular imaging with a phase of the cardiac cycle by using electrocardiography signals to time the image acquisition and thereby provide images with consistent positions of anatomical features and to allow more accurate minimally invasive procedures. A comparable, clinically practical, real time signal of respiratory phase or internal organ position that can be used with CT or MR has not been available to date. It is especially problematic in the patient who is breathing voluntarily and not intubated with an endotracheal tube where volume input may be controlled. Normal respiration is a complex mixture of diaphragmatic and chest wall movements that may vary from breath to breath. The result is that a similar breath may not result in a similar position of internal organs that move with respiration. New minimally invasive ablative techniques such as (RF) radio frequency and cryogenic ablation require very accurate probe placement to simultaneously allow effective treatment and avoid injury to surrounding structures. Accurate respiratory gating is essential for accurate instrument placement in organs or structures that move with respiration and, in many cases, is the sine qua non of these treatment modalities. One method of respiratory gating proposed herein is to use real time ultrasound to monitor the position of the diaphragm or an organ moving with respiration throughout a procedure. For example, as the patient holds his breath for the targeting CT image(s), a "snapshot" ultrasound image of the diaphragm or other surrogate organ is also obtained. The ultrasound transducer is held against the patient in a fixed position throughout the procedure by the instrumentation described in the present invention. The patient is then withdrawn from the scanner gantry and an angle of approach and entry point on the skin is chosen. The site is suitably prepped and sterile drapes are placed if not already done. Then, either on his own or with coaching, the patient is able to watch the real time ultrasound image and breathe to the point of perfect overlap or coincidence with the earlier "snapshot" image, and then hold his breath at that point while the instrument is placed. Ideally this will result in perfect correlation of the patient's real time anatomy with the previously obtained CT image. The clinical result will be fewer sticks to achieve the ideal placement of instruments, saving time and patient morbidity. The key to success using this method is that the ultrasound transducer must remain in an absolutely fixed relationship to the patient throughout the imaging and instrument placement phases of the procedure. The present invention makes this both possible and practical.

Thus, there is a need for technology that functions within the imaging environment and addresses the problems associated with respiratory gating.

The ability to choose points in space that can be fixed relative to the patient or some part of the patient's anatomy for holding instruments, medical support equipment and patient positioning devices in a desired fixed orientation and location is fundamental to surgical and medical practice. While standard operating tables, for example, may be fitted with a broad range of accessories and attachments to facilitate a wide array of operations, the versatility and convenience provided by such a standard operating table is currently unavailable for use during CT or MR imaging using the supports currently employed therewith.

There is a need for a system that can offer many of the functions of a standard operating table when a patient is on a scanner tray. There also is a need for accessories that cooperate with the scanner tray to increase the accuracy of targeting, instrument positioning and guidance in an imaging environment.

Finally, there is a need for a versatile emergency stretcher that can carry a patient through multiple medical environments during resuscitation, diagnostic evaluation and initial treatment without risking further injury to the patient or emergency personnel that may come from the physical handling that traditionally has been required.

SUMMARY OF THE INVENTION

The invention relates to a system for supporting a patient during computed axial tomography imaging including a movable platform formed of a radiolucent material, a discrete attachment region in the platform, and a curvilinear articulating arm coupled to the platform at the discrete attachment region. The system may further include an end effector demountably attached to the articulating arm. The end effector may be a clamp, a bracket, or a linear instrument guide. The system may further include an ultrasound transducer supported by the end effector. In addition, the system may include a cushion.

The platform may have a plurality of openings forming hold regions disposed proximate a cranial end and a caudal end thereof. A plurality of discrete attachment regions may be provided in spaced arrangement proximate the perimeter of the platform. In some embodiments, the platform may have a central arcuate portion disposed between a pair of ledge portions. Also, in some embodiments, the at least one discrete attachment region may be a threaded insert.

The curvilinear articulating arm may include a plurality of ball and socket connections. In some embodiments, the curvilinear articulating arm may include a plurality of balls and sleeves disposed on a tensioning wire. The curvilinear articulating arm may be coupled to the platform with a first handle associated with the discrete attachment region, and the first handle may include a pivotable lever for adjusting tension of the tensioning wire to vary flexibility of the curvilinear articulating arm.

The invention also relates to a method for supporting a patient during a plurality of procedures including: disposing the patient on a movable platform formed of a radiolucent material; positioning a device with respect to the patient, the device being disposed on a curvilinear articulating arm coupled to the platform; placing the platform, positioned device, and patient in a computed axial tomography imaging system and performing an imaging procedure; supporting the platform with the patient thereon on an operating room table and performing a surgical procedure. The platform may be disposed on a separate imaging system table while performing the imaging procedure. The positioned device may be maintained in substantially the same position during the imaging and surgical procedures. The method also may include supporting the platform with the patient thereon on a hospital bed. In addition, the method may include supporting the platform with the patient thereon on a stretcher. The device may be an ultrasound transducer, a probe, or a needle. Further, the method may include disposing a cushion between the patient and the platform, the cushion being conformable to anatomical contours of the patient. Moreover, the method may include coupling the platform to an electrohydraulic system for positioning and orienting the platform.

The present invention additionally relates to a method for supporting a patient during a plurality of procedures including: disposing the patient on a movable platform formed of a radiolucent material; positioning a device with respect to the patient, the device being disposed on a curvilinear articulating arm coupled to the platform; placing the platform, positioned device, and patient in a computed axial tomography imaging system and performing an imaging procedure; performing a surgical procedure while the platform, positioned device, and patient remain in the computed axial tomography imaging system.

Also, the present invention relates to a movable platform is provided for supporting a patient in multiple medical environments such as during computed axial tomography imaging and surgery. The platform may have at least one discrete attachment region formed therein for coupling the platform to another component.

The present invention further relates to providing a base platform and accessories that may enable efficient use of a CT or MR scanner in new and more complex minimally invasive surgical procedures. An exemplary system for use in this environment includes a platform or scanning tray and a set of manual devices that may achieve accurate and reliable positioning of a patient and/or required medical equipment that may move with the patient on the scanning tray. Such a tray also may serve as a fail-safe, manually controlled backup to the more sophisticated computer guided devices in procedures where accurate and stable equipment positioning are essential to success.

Optimally, the base platform may be designed to standardize and simplify indexing of the patient (or a patient's anatomy) to the imaging scanner and may simplify and speed up the process of image and equipment registration for image guided surgeries.

The surgical tray (platform) preferably does not interfere with image acquisition, may pass through the imaging ring/gantry of a scanner, may serve as a stable platform for the patient to lie upon, may be fitted with a mattress for patient comfort and positioning, may securely support a patient in a stable and relatively fixed position, may allow for selective support of individual extremities in a desired fixed position, may be keyed to acquired images and remain in a fixed relationship to a pre-existing scanner table and/or tray, and may have multiple or infinite locations around its perimeter for the secure attachment of lockable positioning arms, medical accessories such as armrests and IV poles and other devices that may be required to perform various procedures.

In one embodiment of the present invention, the platform is a separate tray that nests into or rests upon the pre-existing table and/or tray of the imaging equipment. Locating features may be provided in readily visible areas of the platform, allowing the platform to be easily indexed to the pre-existing table and/or tray. In some embodiments, the tray may be tiltable (Trendelenburg or reverse Trendelenburg positions), may be rolled in either direction and may be elevated independently of the pre-existing table and/or tray.

One or more lockable positioning arms with end effectors provided on a free end thereof may be coupled to the platform for various grasping, guiding and instrument stabilizing functions. An end of the lockable positioning arm may be fixed to the perimeter of tray at discrete locations provided for coupling, while the free end may be configured to receive a variety of end effectors. The lockable positioning arms may move with six degrees of freedom. Manually powered or externally powered locking mechanisms may be provided to arrest, limit, or provided resistance to motion of the arm.

In some embodiments, the arms may be designed and orientable to be passed with a patient into or through the gantry of the CT and/or MR scanner. The arms may be constructed of materials that are safe in the imaging environment and that will not interfere with the acquisition of images that are required for the procedure.

End Effectors that attach to the free end of the positioning arms may be sterilized and reusable or made as single use sterile disposable attachments. It may be desirable that the connection mechanism of the end effectors to the arms be a proprietary design (such as the one shown in figures herein). The end effectors may either include or accommodate a sterile sleeve type cover/drape to cover the positioning arm. Examples of end effectors that may be used include a clamp and a bracket to hold an ultrasound transducer that may be used to facilitate a procedure. For example, it may be used to monitor the position of internal organs during respiration (such as the diaphragm).

Another end effector or device for coupling to the platform may be an instrument positioning/guidance device that may be provided for holding and permitting the accurate translation of a linear instrument along the path of its axis. Such a guidance device may be configured to function with a wide range of linear instruments (e.g., cryotherapy probes, RF probes or needles) and have user adjustable drag (frictional resistance) to advancement or withdrawal. Such a device also may be configured to function with a software driven computer assisted tracking/targeting system that may be integral with the scanner.

A general purpose grasping clamp may be coupled to the platform for holding a variety of surgical instruments such as retractors, laparoscopes and laparoscopic instruments.

Other devices for coupling to the platform may: hold or function as a template grid for spaced apart parallel linear instrument placement; hold or function as a stereotactic device that may have micro-adjustment capability; function as a linear instrument driver with remote operator control; or may have locating features that could function with computer driven guidance systems (e.g., infrared or electromagnetic sensors) that may be integrated with the primary imaging system (e.g., the CT or MR scanner) or a single image.

Devices for positioning and maintaining the position of the patient with respect to the platform may be provided such as a shape conforming mattress (e.g., a beanbag-type mattress that may be formed around the anatomic area of concern, with a vacuum applied to the mattress to set the desired shape), arm rests, leg rests, head rests and other components to secure immobilization of various areas of anatomy.

Devices such as a bubble level may be attached to or embedded in the tray to enable a standard orientation within the scanning environment that may facilitate instrument guidance. For example, a transverse bubble level located at the end of the tray may permit accurate leveling of the parallel side surfaces and inserts. A rectilinear bridge across the tray connecting these surfaces and inserts for example incorporating a protractor oriented in this transverse plane, may then be used to determine a precise angle of approach in a transverse plane that may correlate with a CT image (note that a scanner may be leveled with a bubble level).

Preferably, the platform of the present invention may be portable and adapted or universal in design for use with many different brands of scanners. Some embodiments of the present invention may be constructed with all components applicable for use with either CT or MR scanners, because of the different requirements of the imaging environments and the potential for interference with image acquisition. Thus, the platform may be formed of a material suitable for use in CT scanner but not MR scanners, or vice versa, or the material may be suitable for use in both imaging environments.

In some embodiments, the perimeter of the platform/tray may be configured to accept equipment for use in the scanner or scanner environment in order to provide additional medical or analytic functions aside from the CT or MR scanning. For example, such equipment may include, but is not limited to, brackets, braces, stereotactic equipment, orthopedic positioning and stabilizing devices and instrument guidance equipment of any type.

Additional accessories may include an adjustable IV pole, armrest(s) and flatbar siderail sections that are the same as or similar to those that typically are found on a standard operating table.

Some platforms of the present invention may include both curved portions and flat portions. The curved portions, for example including a concave section, may be configured to retain a patient and may have a radius of greater than about 50 cm, greater than about 60 cm, or greater than about 70 cm. Flat portions may be provided proximate the edges of the platform and may form flanges configured to hold supplemental medical equipment. The flat portions may be parallel to one another and coplanar, allowing ease of positioning of medical equipment along the perimeter of the tray. In addition, the flat portions along the edges of the tray may be coplanar with a plane of travel of the tray within the scanning instrument. In some embodiments, the flat portions may be at least about 10 mm wide, at least about 20 mm wide, at least about 30 mm wide, or at least about 40 mm wide. The flat portions may extend away from the centerline of the tray on a plane spaced from the lowermost portion of the tray, thus allowing room to fasten through or around the edges of the tray by providing access to the underside thereof. The tray may be 10 mm or less in thickness at its curved portions, or may be less than 25 mm thick throughout. The tray instead may vary in thickness.

In some embodiments, the tray may contain coupling portions or holes configured to receive supplemental medical equipment. The holes may be threaded in some embodiments, or may have threaded inserts therein. The holes may allow rapid manual fixation of supplemental medical equipment and also may not interfere with image acquisition. In another embodiment, the edges of the tray may be configured as a rail, thus permitting a user an infinite choice of positions for instrument fixation as compared to a fixed number of defined points provided by threaded holes. Such a rail may be provided with teeth and function as a gear rack for permitting encoded motion of an arm or guidance device along its length.

A demountable tray may permit a patient to be placed in Trendelenburg position if desired by lifting the end thereof.

Additional components of the tray may include one or more flexible or articulated arms that may be placed at various desired points along either side or end of the tray. The arms may be configured to be removable from the tray and movable or repositionable along the perimeter thereof. In some embodiments, a free end of an arm may be manually positionable and able to hold a desired position when set by a user. The arms may function with several modes of resistance. For example, a low resistance mode may permit easy manipulation of the free end, and a locked mode may establish a fixed point in space with adequate resistance to movement to hold a steady position for a wide range of medical instruments (e.g., hold 10 pounds of weight without loss of position). In some embodiments, the arms may have a quick-release function at the end fixed to the tray that permits a user to easily remove the arm from the tray or reposition it along the perimeter of the tray. Multiple arms may be configured to join together at the free ends thereof for added stability or increased functionality of a grouping of instruments, either bridging over the patient between two or more edges of the tray, or extending from only one side thereof. Also, the arms may be dimensioned and configurable so as to conform closely to the body of a patient and not interfere with patient movement through the scanner while holding a given position.

In some embodiments, the components coupled to the tray such as articulating arms may be relatively non-conductive to electricity and non-ferrous, so that the components are not affected by a magnet or motion within a magnet. Also, in some embodiments the arms may be relatively radiolucent. Suitable materials for such components that may be placed in the imaging plane includes various plastics, resins, and composite materials, in addition to titanium, aluminum and some metal alloys and will vary depending on whether the imaging modality is CT or MR.

In some embodiments, the arms may be configured to have one or more end fittings that permit various instruments or devices to be attached or grasped. The end fittings may be detachable, easily sterilized and function with a sterile sleeve type drape to also cover the arm(s). In some embodiments, the end fittings may be pre-sterilized single use parts with a sterile sleeve type drape already attached thereto.

For some procedures, an arm may be provided with position encoders in the joints thereof for integrating the position of the arm or an instrument attached to the arm with an image recorded by the scanner. Such an arm may be anchored to a fixed location on the tray and subsequently indexed to the CT or MR image. Thus, an indexing capability of the tray and the arms with the imaging plane of the scanner may be provided.

In another embodiment the tray may be configured with handhold cutouts in each end. Also, handles may attach along the sides of the tray that may also function as locations for straps that can secure the patient to the tray. Thus, the tray may also function as a temporary stretcher and be used to transport a patient within an emergency medical environment. A device may be mounted to the tray that provides strain relief for ventilation tubing when a patient has an endotracheal tube in place. An IV pole may be mounted to the tray. Thus, the tray and attachments are configured to facilitate movement of a patient from an ambulance to a guerney and from a guerney to a CT scanner table where appropriate x-rays may be taken, and then from the CT scanner table back to a guerney and onto an OR table without having to physically handle or move the patient independent of the tray.

Thus, the invention relates to a tray configured for holding a patient within a scanning instrument or when the need for placement into a scanning instrument is likely, the tray including a surface configured to retain a patient, and a means for securing supplemental medical equipment along the edges of the tray. The surface configured to retain a patient may be concave. Also, the tray may contain a first edge and a second edge, and a plurality of holes along the first and second edges, with the holes being configured to receive supplemental medical equipment. The holes may be threaded. Third and fourth edges or ends may have handhold cutouts. Removable arms may extend from the surface of the tray. Further, the tray and supplemental medical equipment may be substantially electrically non-conductive. The tray and supplemental medical equipment may be substantially radiolucent. In some embodiments, one or more portions of the present invention may be radiopaque.

BRIEF DESCRIPTION OF THE DRAWINGS

Preferred features of the present invention are disclosed in the accompanying drawings, wherein:

FIGS. 5H to 5J show an interface portion for coupling end effectors to the free handle of FIG. 1, including (5H) a perspective view, (5I) a first side view, and (5J) a second side view;

FIG. 8 shows the rail assembly of FIG. 1, including (8A) a perspective view, (8B) a first side view, and (8C) a second side view;

FIG. 10 shows the arm board of FIG. 1, including (10A) a bottom perspective view, and (10B) a top view;

FIG. 11 shows a lift beam assembly for use with the support system according to the present invention, including (11A) a perspective view, and (11B) a side view;

DETAILED DESCRIPTION OF THE PREFERRED EMBODIMENTS

Terms such as "cephalad," "caudal," "upper" and "lower" as used herein are provided as non-limiting examples of the orientation of features.

Figure 1:
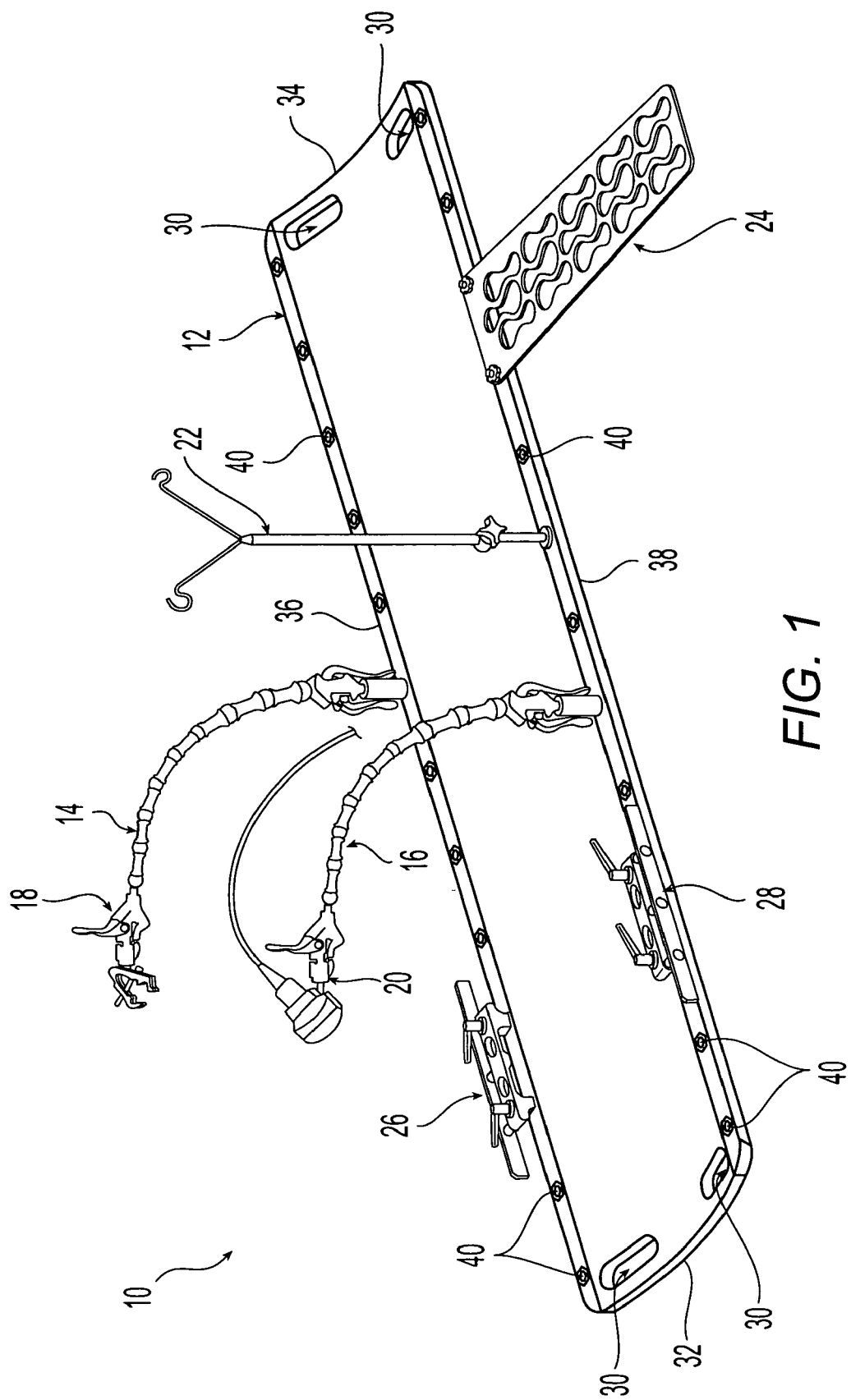
FIG. 1 is a perspective view of a support system according to the present invention.

Referring initially to FIG. 1, a support system 10 according to the present invention is shown with a variety of components coupled thereto. Support system 10 includes a tray 12, curvilinear articulating arm assemblies 14, 16, end effectors 18, 20 coupled to arms 14, 16, IV pole 22, arm board 24, and rail assemblies 26, 28. A variety of end effectors may be demountably attached to the ends of arms 14, 16 to assist a technician or practitioner with a medical/imaging procedure or provide other features useful with respect to a patient. End effector 18, for example, is configured as a bracket or clamp, while end effector 20 is configured as a self-centering abdominal probe bracket.

In a preferred exemplary embodiment, tray 12 includes two pairs of hold regions 30, each pair being disposed proximate a free cranial end 32 or free caudal end 34 of tray 12. In alternate embodiments, other numbers of hold regions 30 may be provided such as two or more, and hold regions 30 may be provided in other regions of tray 12 such as intermediate ends 32, 34 proximate sides 36, 38. Hold regions 30 may be configured as hand holds, or alternatively may be configured to receive strapping so that tray 12 may be releasably coupled to another object such as an ambulance stretcher, hospital bed, operating room table, or imaging scanner table. As also shown in FIG. 1, attachment regions 40 are provided proximate sides 36, 38 for demountably coupling components such as curvilinear arms 14, 16, IV pole 22, arm board 24, and rail assemblies 26, 28 to tray 12, as will be further described below. In the exemplary preferred embodiment, tray 12 is provided with thirteen attachment regions 40, although in alternate embodiments other number of regions 40 may be provided such as at least one.

Figure 2A:
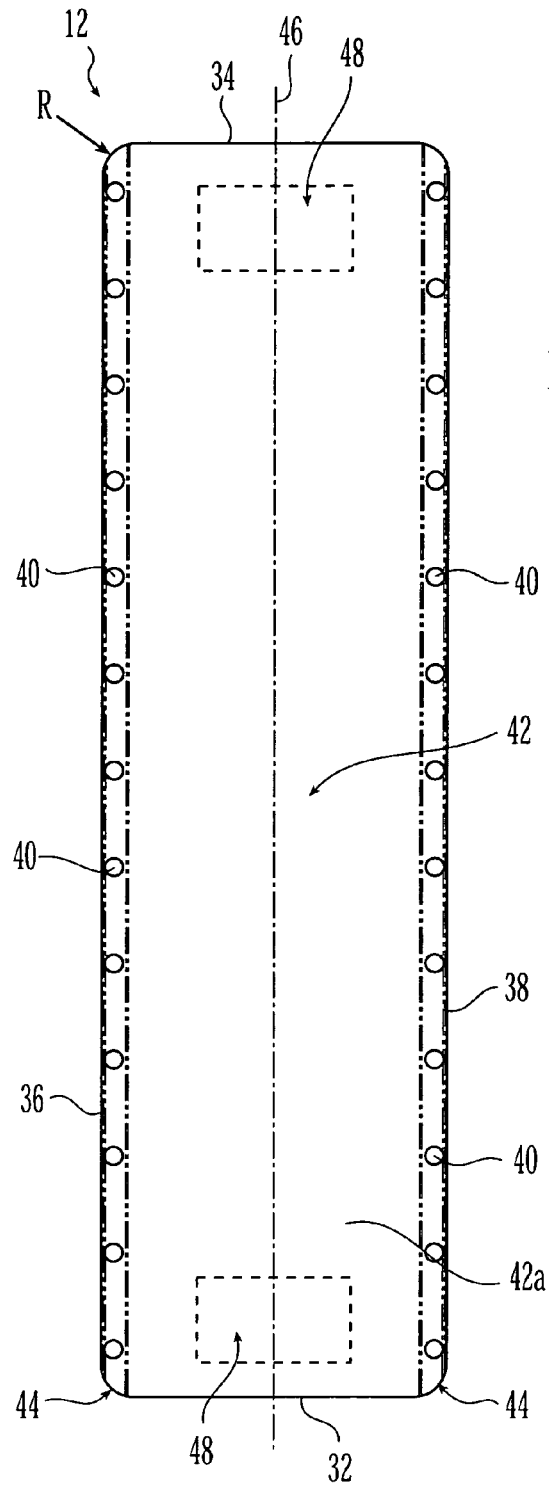
FIG. 2 shows the tray of FIG. 1, including (2A) a top view, (2B) a cross-section taken perpendicular to the central axis of the tray, and (2C) a partial cross-section showing detail taken at IIC.
Figure 2B:
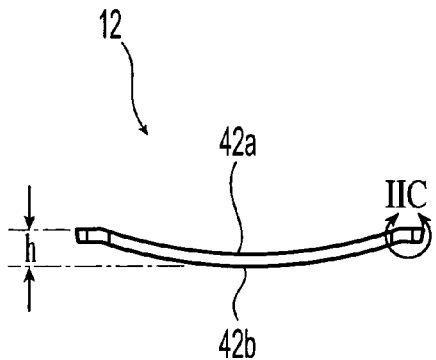
Figure 2C:
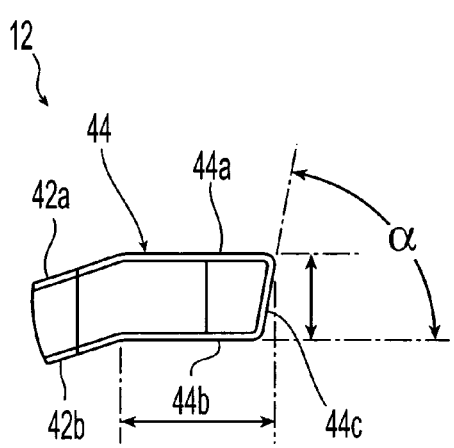

Turning to FIGS. 2A-2C, additional features of tray 12 are shown. Although hand hold regions 30 are not included in the figure, such regions may be provided as shown in FIG. 1. Attachment regions 40 are provided in spaced arrangement along the perimeter of tray 12. Preferably, tray 12 includes a central arcuate portion 42 disposed between outer ledge portions 44. Preferably, regions 40 are provided on outer ledge portions 44. Central arcuate portion 42 preferably has an upper concave surface 42a for receiving a patient and optionally a cushion (not shown) for the patient to rest against, and optionally includes a lower convex surface 42b. Preferably, outer ledge portions 44 include upper and lower surfaces 44a, 44b connected by a sidewall 44c at an angle α with respect to surface 44b. In a preferred exemplary embodiment, sidewall 44c is disposed at an angle α between about 60° and about 100°, more preferably between about 70° and about 90°, and most preferably at about 80°.

In a preferred exemplary embodiment, tray 12 is formed of natural finish carbon fiber, R-51 foam core, and phenolic. Attenuation preferably is less than 1 mm A1 equivalency. Thus, tray 12 is radiolucent and suitable for use with CT scanners. In other embodiments, tray 12 is formed of a material suitable for use with MR scanners. In addition, tray 12 preferably supports a load of 900 lbs. evenly distributed along centerline 46, about which tray 12 may be substantially symmetric as shown. Indicia 48 optionally may be provided, as shown for example proximate ends 32, 34. The indicia may for example indicate preferred orientation of tray 12 with respect to a patient lying thereon.

In the preferred exemplary embodiment, attachment regions 40 on each side of tray 12 are evenly spaced from each other by about 6 inches between centers thereof. To accommodate patients and equipment attached to tray 12, in one preferred embodiment tray 12 has a length of about 78 inches, a width of about 21 inches, a generally uniform thickness of about 0.9 inch, and a height h of about 2.5 inches. Corners may be provided with a radius R of about 2 inches. In the preferred exemplary embodiment, attachment regions 40 preferably accommodate threaded inserts, which may be formed of aluminum.

In some embodiments, tray 12 is sized to hold an adult patient, and may be between about 180 cm and about 200 cm long. However, it will be appreciated that longer and shorter trays may be provided. In order to accommodate an adult patient, tray 12 may support an overall weight capacity of at least about 200 pounds, and preferably at least about 300 pounds. However, if a tray 12 is sized for use with a pediatric patient, tray 12 may only accommodate weights that do not exceed 200 pounds, and more preferably do not exceed 100 pounds.

Although the surface of portion 42 of tray 12 is substantially smooth in the preferred exemplary embodiment, in alternate embodiments the surface may be textured to provide additional resistance to motion of objects and/or a patient placed thereon.

Tray 12 thus is suitable for use in multiple environments, and thus may "move" with the patient from one environment (e.g., ambulance) to the next (e.g., CT scanner) without removing a patient supported thereon.

Figure 3A:
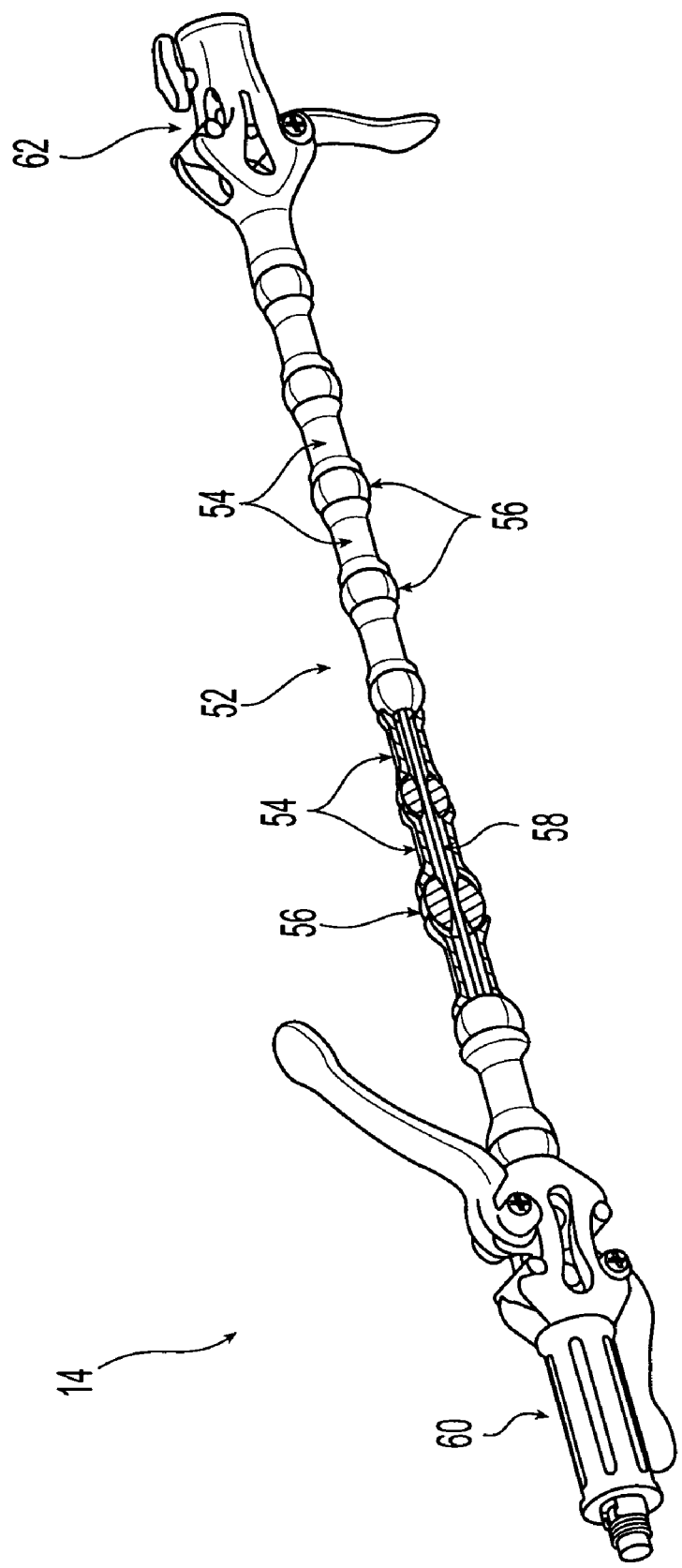
FIG. 3 shows the curvilinear articulating arm assembly of FIG. 1, including (3A) a partial cross-sectional perspective view, and (3B) a side view.
Figure 3B:
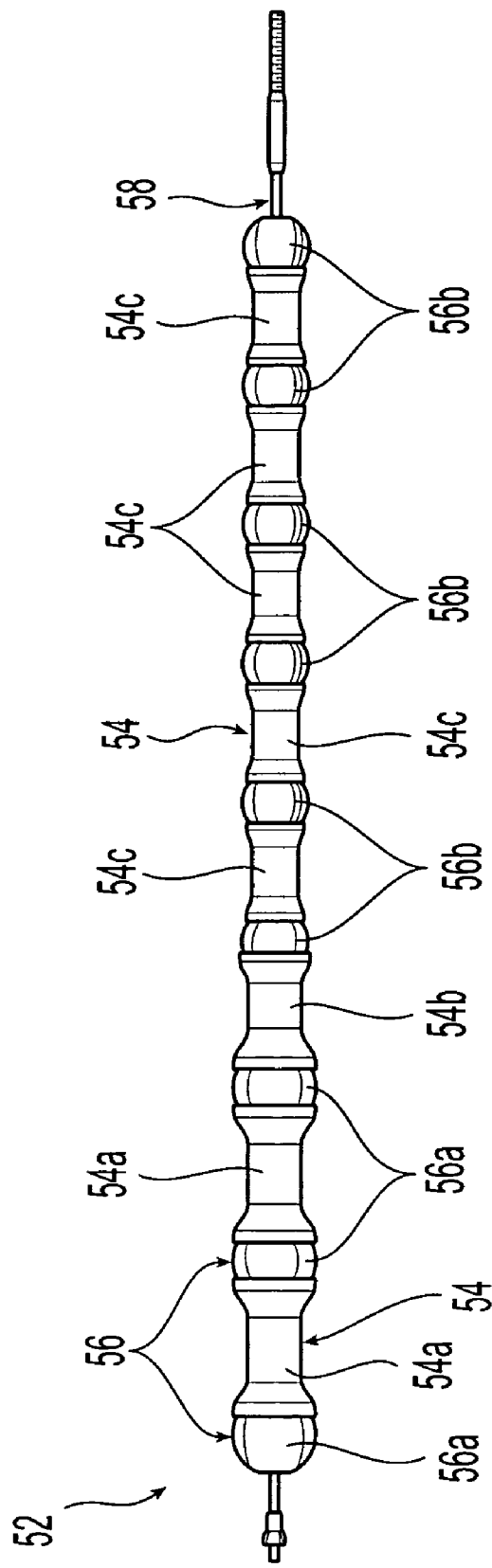
Figure 4A:
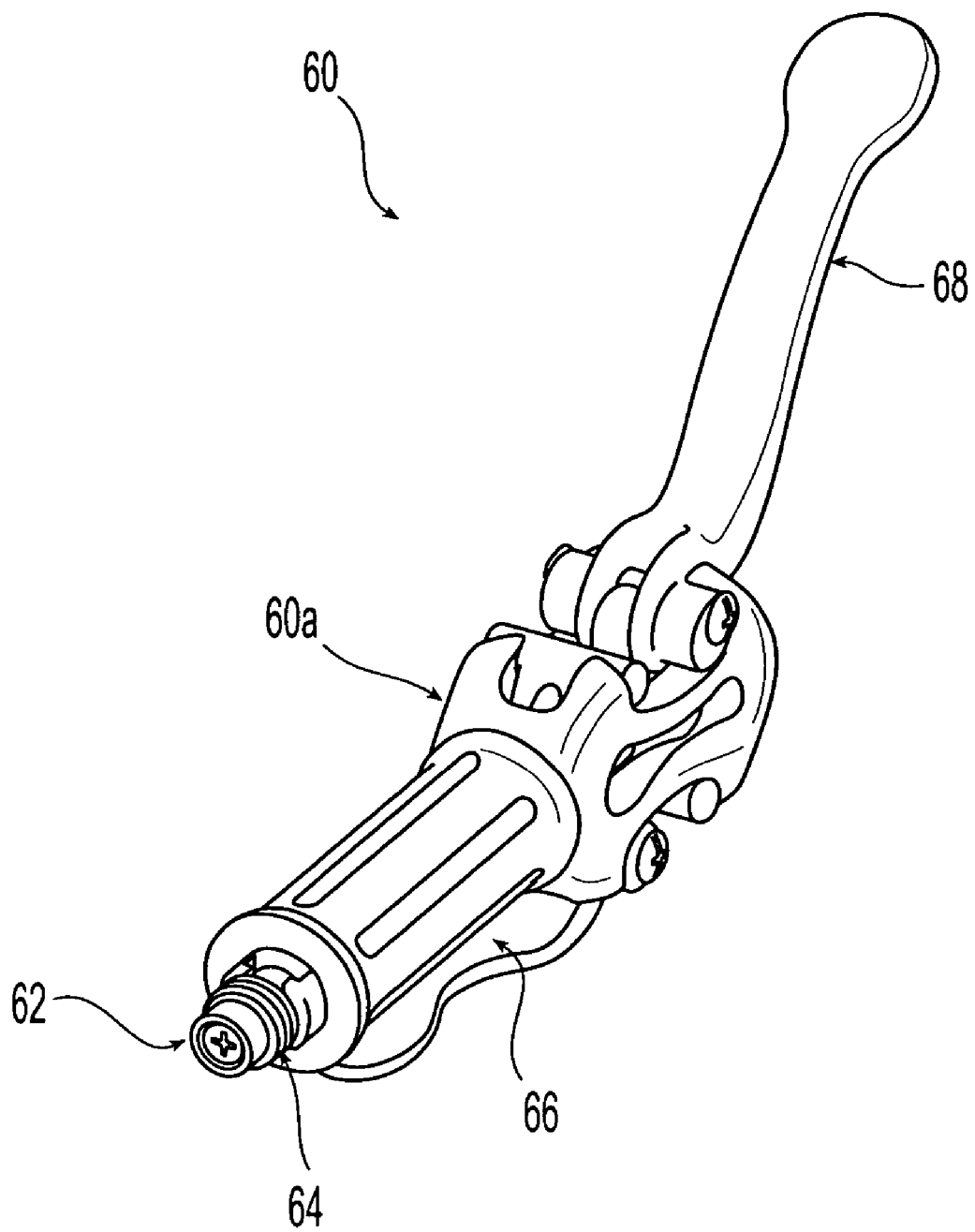
FIG. 4 shows the base handle of FIG. 1, including (4A) a perspective view, (4B) a bottom view, (4C) a top view, (4D) a first side view, (4E) a second side view, (4F) a front view, and (4G) a back view.
Figure 4B:
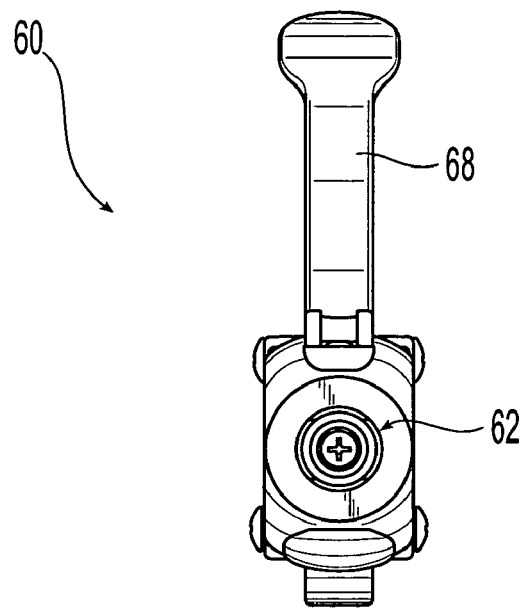
Figure 4C:
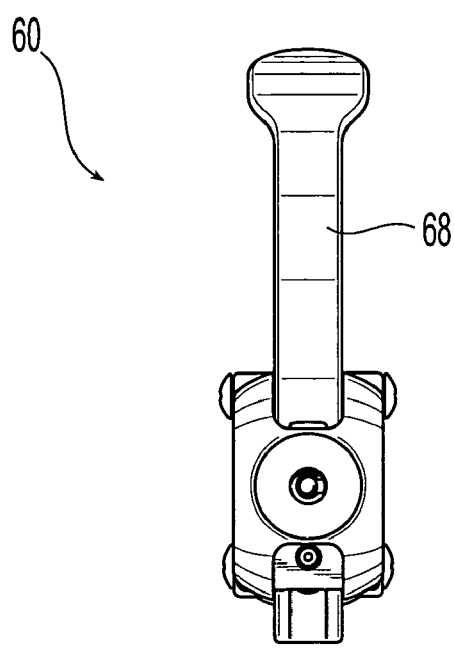
Figure 4D:
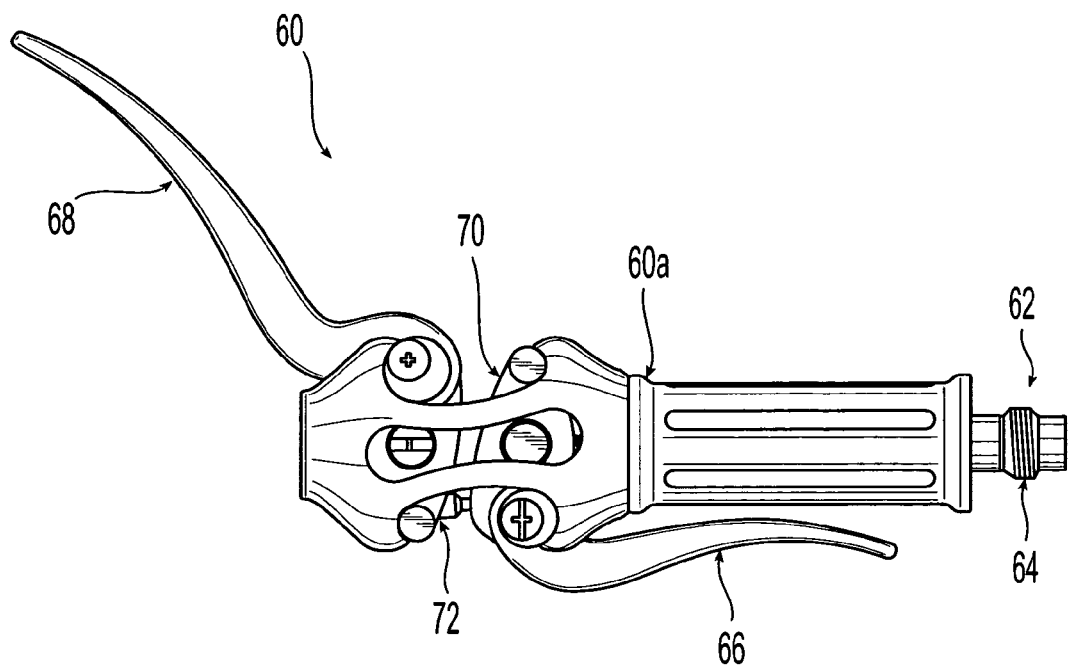
Figure 4E:
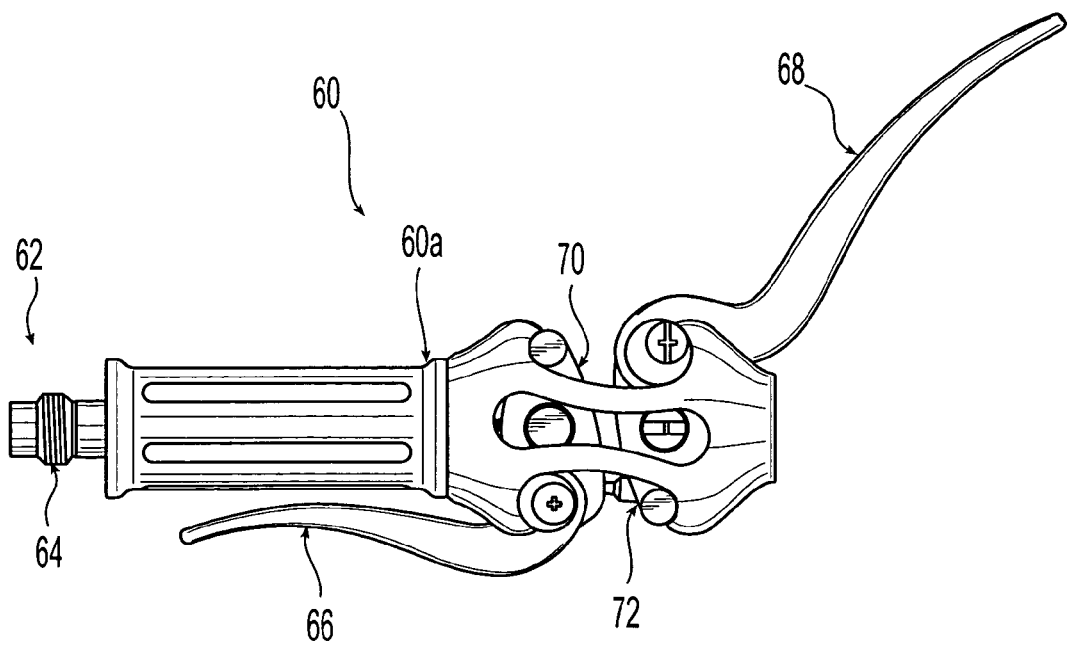
Figure 4F:
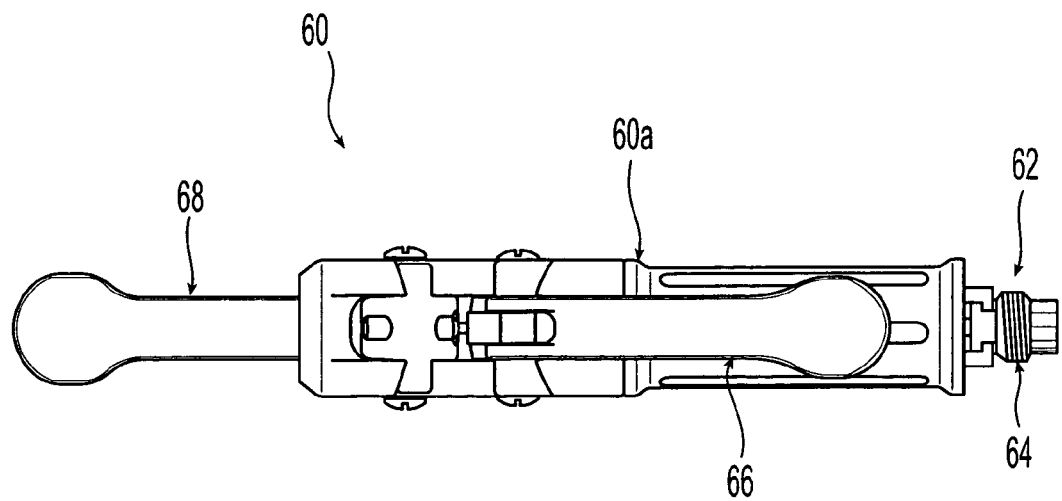
Figure 4G:
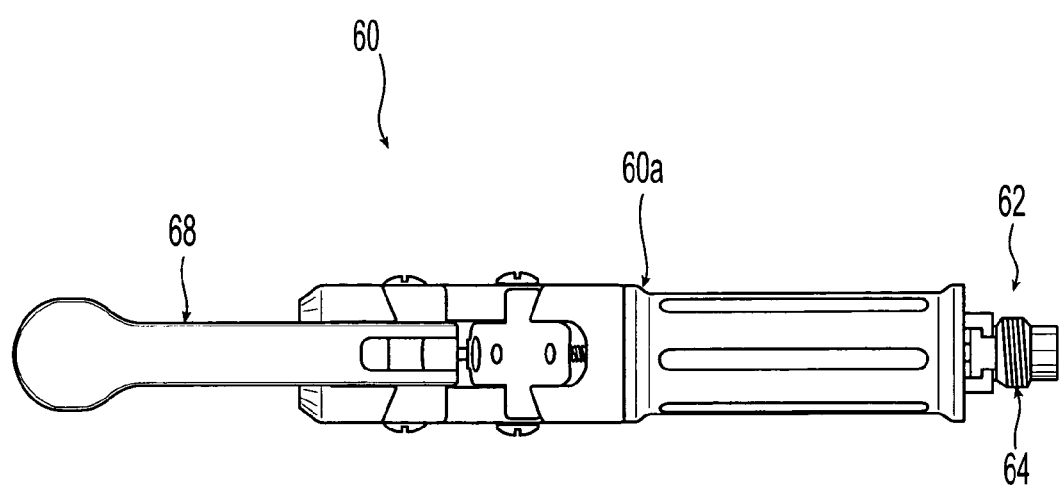

Turning to FIG. 3, a curvilinear articulating arm assembly 14 is shown in partial cross-section. Arm assembly 14 includes a central arm 52 with a ball-sleeve arrangement that forms joints. In particular, central arm 52 includes a plurality of sleeves 54 with spherical balls 56 disposed therebetween thus forming ball and socket connections. In the preferred exemplary embodiment, three balls 56a of a first size are disposed adjacent one another proximate one end of arm 52, while the remaining balls 56b are of a second size smaller than the first size. Sleeves 54a of a first size and sleeves 54c of a second size smaller than the first size are provided for accommodating balls 56a, 56b, respectively, while a transition sleeve 54b is provided intermediate sleeves 54a, 54c as shown for accommodating a ball 56a on one side and a ball 56b on the other side thereof. As shown in FIG. 3A, sleeves 54 are configured and dimensioned to receive balls 56a, 56b at ends thereof and thus permit articulating of sleeves with respect to each other. A tensioning wire 58 runs generally centrally through sleeves 54 and balls 56, as will be further described shortly. Preferably, wire 58 is formed of metal. One exemplary operation of a wire tensioning mechanism is shown and described in U.S. Pat. No. 3,858,578 to Milo, which is expressly incorporated herein by reference thereto. Preferably, curvilinear articulating arm assembly 14 may move with six degrees of freedom.

A base handle 60 is coupled to central arm 52 on a first end thereof, preferably adjacent a ball 56a. In addition, a free handle 62 is coupled to central arm 52 on a second end thereof, preferably adjacent a ball 56b.

Turning to FIG. 4, base handle 60 will be described. Base handle 60 includes a coupling 62 for demountable coupling to tray 12. In the preferred exemplary embodiment, coupling 62 comprises a threaded portion 64 which may be threadably received in a threaded insert (not shown) disposed in an attachment region 40 of tray 12. Coupling 62 may be threadably associated with an attachment region 40 of tray 12 (via a threaded insert therein), so that arm assembly 14 may be demountably attached to tray 12. Actuation of a first lever 66, which is pivotably associated with handle 60, permits a user to apply a force on coupling 62 so that movement is resisted (e.g., in response to an 8 or 10 pound force applied to arm 52). A second lever 68 also is pivotably associated with base handle 60 and preferably is coupled to tensioning wire 58 so that actuation of second lever 68 may increase or decrease the tension in wire. 58 as desired. By increasing tension in wire 58, central arm 52 preferably becomes less flexible. Thus, a user may orient curvilinear articulating arm assembly 14 as desired, and then increase the tension of wire 58 so that the orientation of arm 52 is releasably fixed. Base handle 60 thus has a body portion 60a, with levers 66, 68 pivotably associated with body portion 60a. As shown for example in FIGS. 4D and 4E, cam mechanisms 70, 72 may be employed with levers 66, 68, respectively.

Next turning to FIG. 5, free handle 62 will be described. Free handle 62 includes a wire receiving portion 80 and an end effector receiving portion 81. In particular, wire receiving portion 80 preferably is configured to receive a ball 56b therein, along with an end of wire 58. As described previously with respect to base handle 60, a pivotable lever 82 is associated with free handle 62 and preferably is coupled to tensioning wire 58 so that actuation of lever 84 may increase or decrease the tension in wire 58 as desired. By increasing tension in wire 58, central arm 52 preferably becomes less flexible. The operation of lever 82 will be described shortly. Thus, a user may orient curvilinear articulating arm assembly 14 as desired, and then increase the tension of wire 58 so that the orientation of arm 52 is releasably fixed. Free handle 62 has a body portion 62a, and lever 82 is rotatable with respect thereto. An interface lock 83 also is rotatably associated with body portion 62a proximate end effector receiving portion 81.

Turning to FIGS. 5H to 5P, an interface portion 84 is provided for coupling end effectors to free handle 62. Interface portion 84 includes a coupling portion 85a in the form of a cylindrical post with a groove 85b formed circumferentially therein. Coupling portion 85a preferably is configured to be received in portion 81 of free handle 62. As now will be described, the bayonet-type mounting provided by free handle 62 permits coupling portion 85a to be releasably engaged and locked to free handle 62. A support portion 85c preferably is integrally formed with coupling portion 85a. Support portion 85c preferably is cylindrical with a diameter greater than coupling portion 85a, and also includes a circumferential groove 85d therein as well as a pair of screws 85e for use in connecting interface portion 84 to the remainder of an end effector. The heads of screws 85e may be received in arcuate recessed portions of body portion 62a proximate end effector receiving portion 81, as shown for example in a petal-like arrangement in FIG. 5B.

Figure 5A:
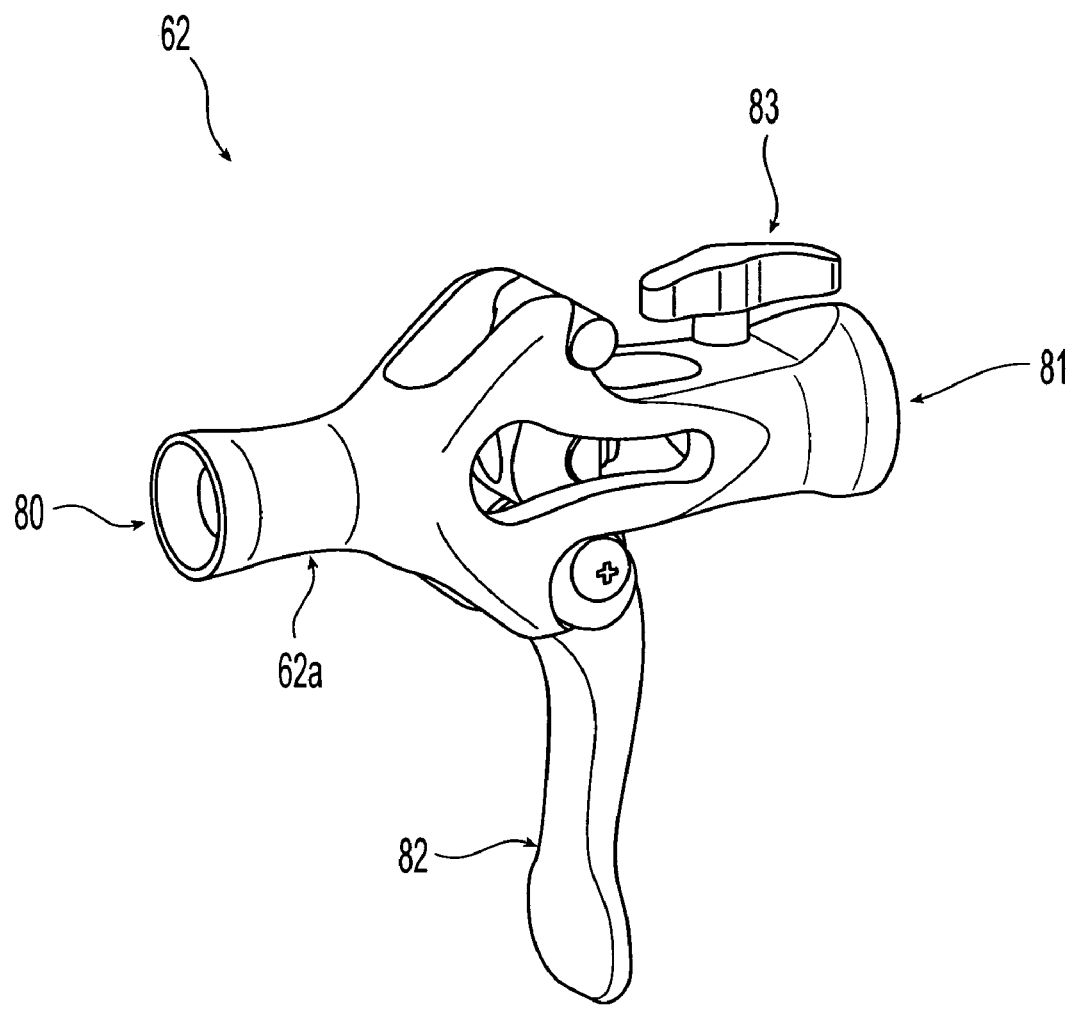
FIGS. 5A to 5G show the free handle of FIG. 1, including (5A) a perspective view, (5B) a top view, (5C) a bottom view, (5D) a first side view, (5E) a second side view, (5F) a third side view, and (5G) a fourth side view.
Figure 5B:
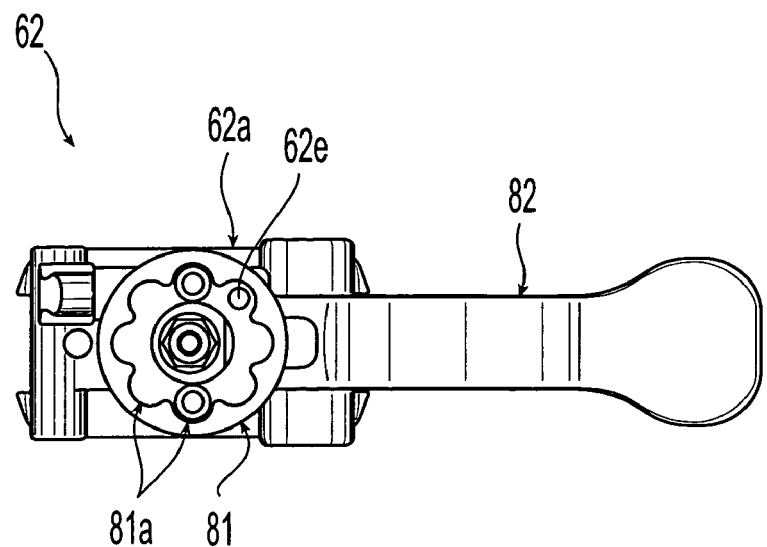
Figure 5C:
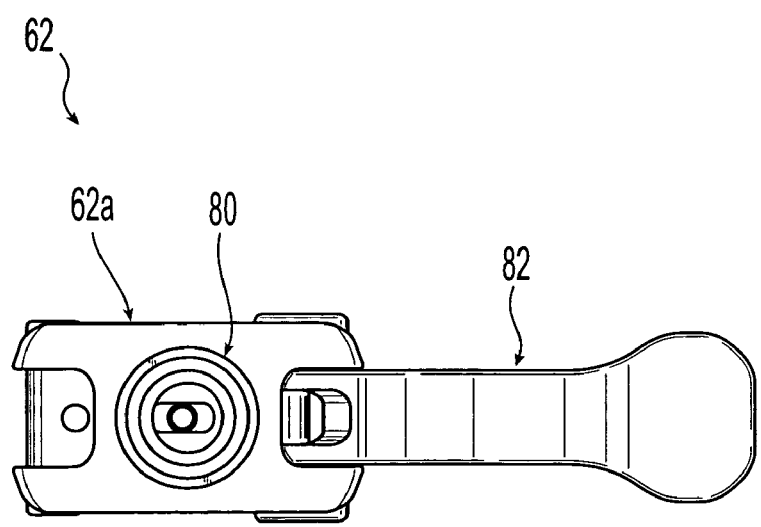
Figure 5D:
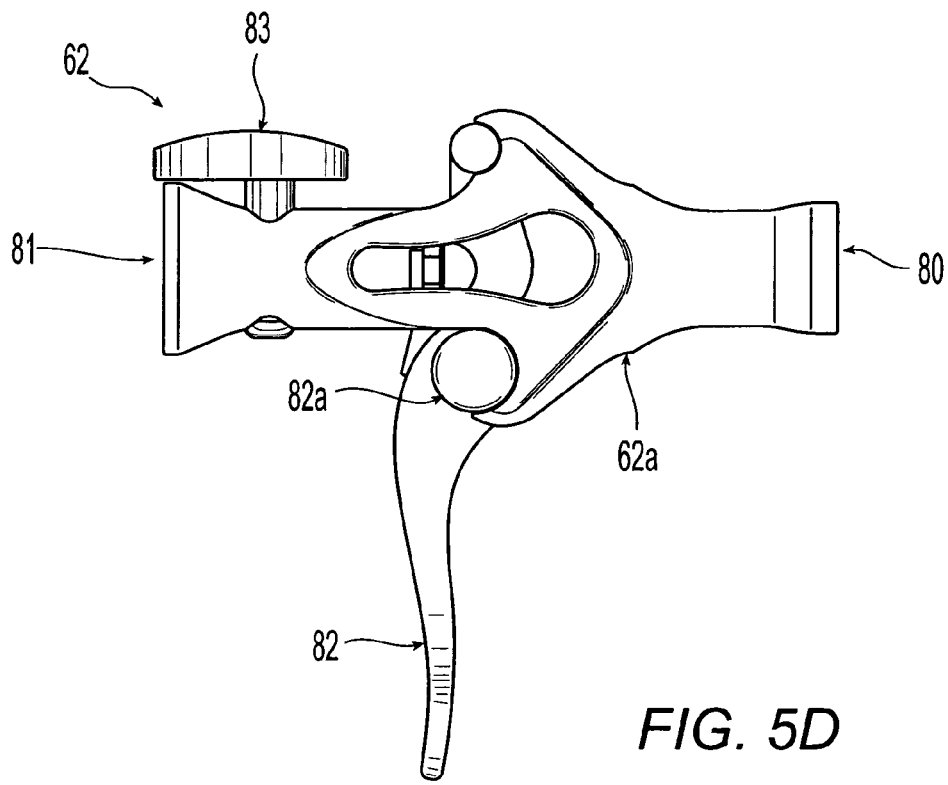
Figure 5E:
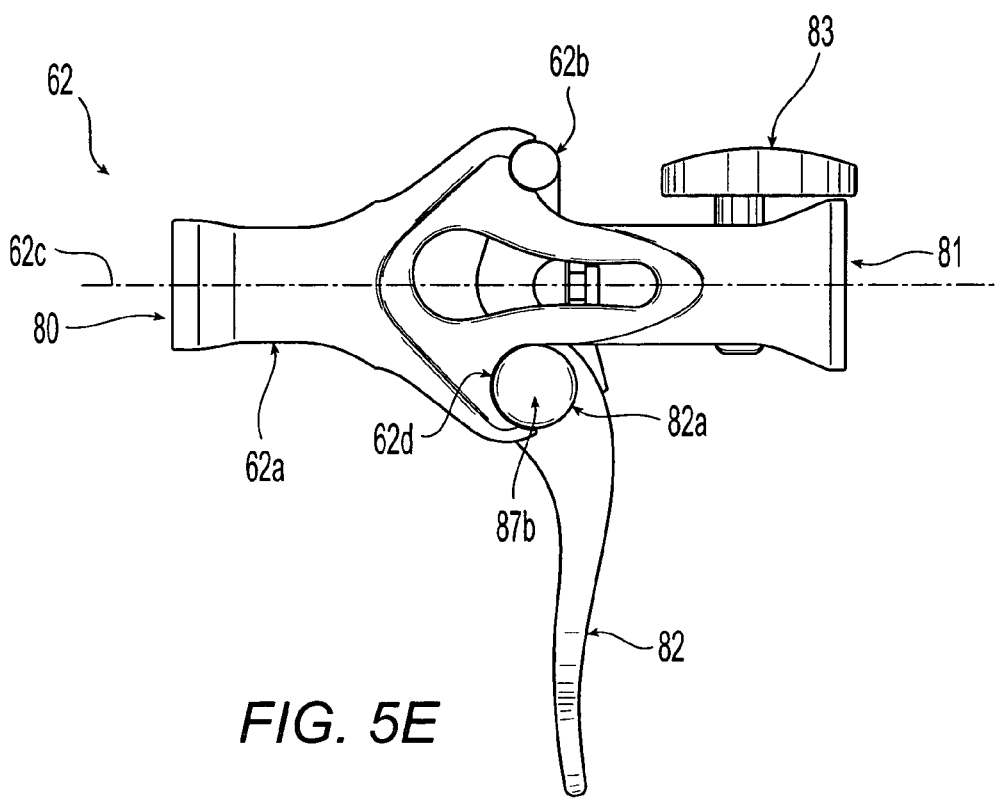
Figure 5F:
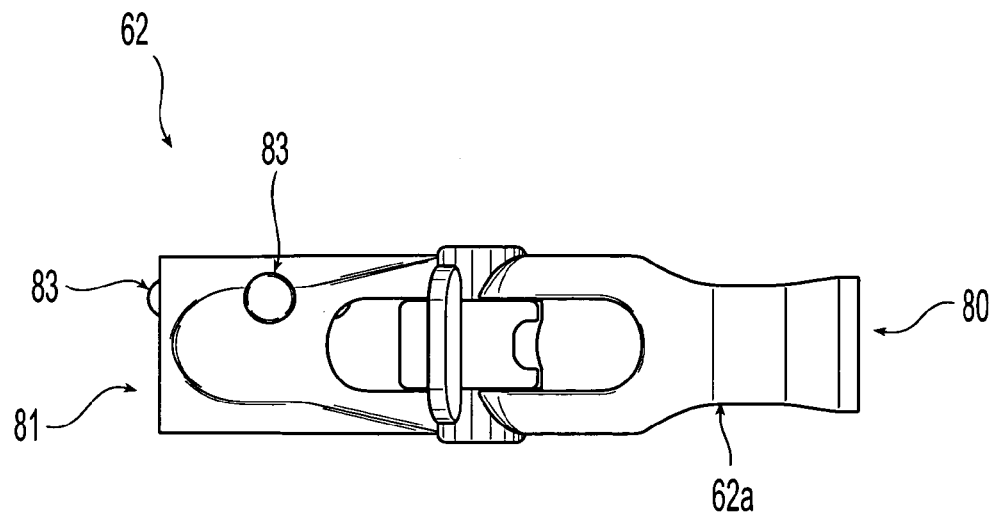
Figure 5G:
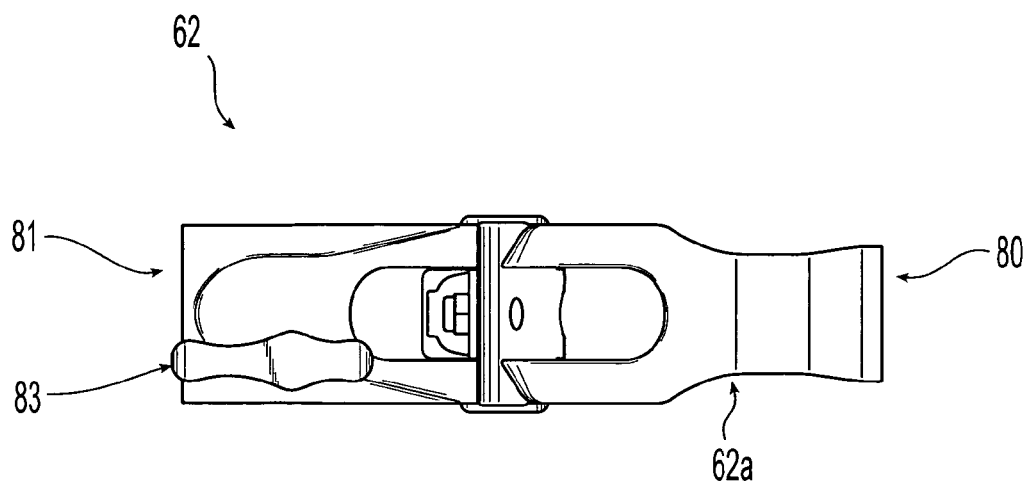
Figure 5K:
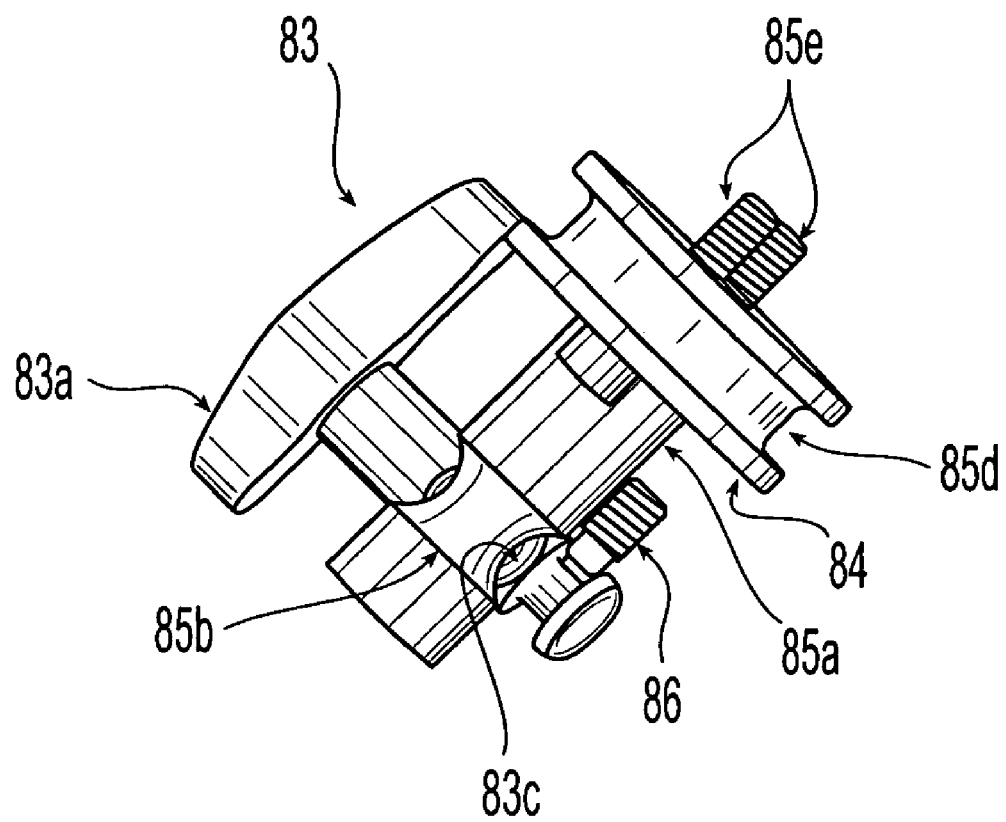
FIG. 5K shows a perspective view of the interface portion of FIG. 5H with a interface lock assembled therewith.
Figure 5L:
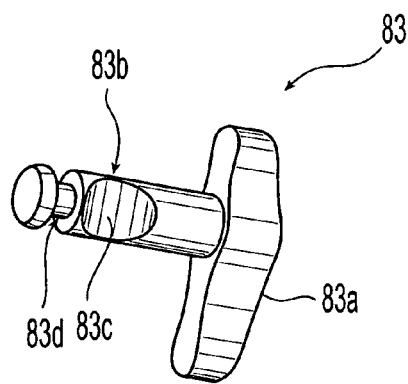
FIGS. 5L to 5P show the interface lock of FIG. 5K, including (5L) a perspective view, (5M) a first side view, (5N) a second side view, (5O) a third side view, and (5P) a fourth side view)
Figure 5M:
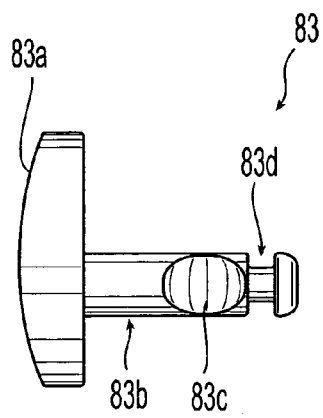
Figure 5N:
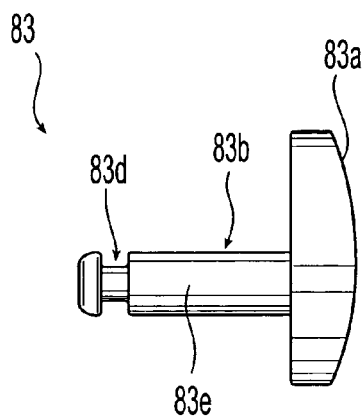
Figure 5O:
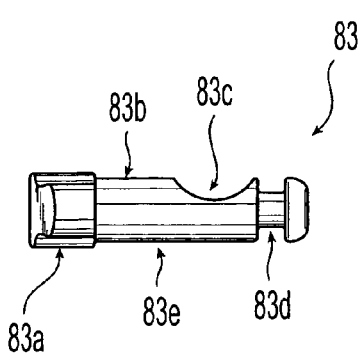
Figure 5P:
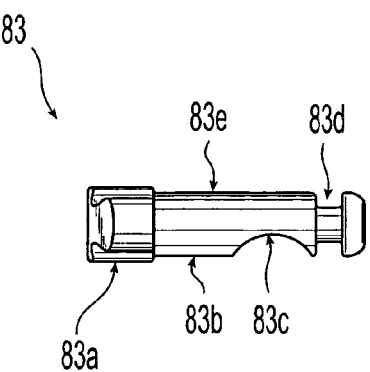
Figure 5Q:
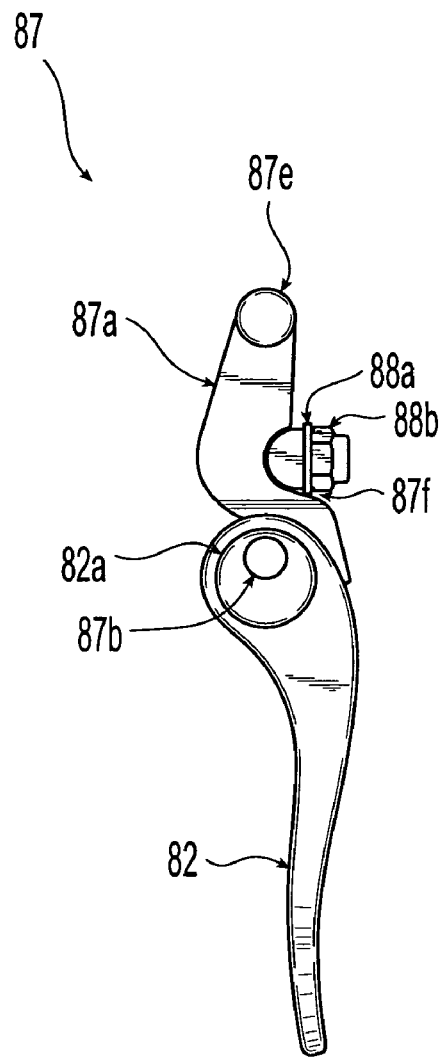
FIGS. 5Q to 5U show a lever of the free handle of FIG. 1 in combination with a rocker arm, including (5Q) a first side view, (5R) a second side view, (5S) a top view, (5T) a bottom view, a (5U) a perspective view.
Figure 5R:
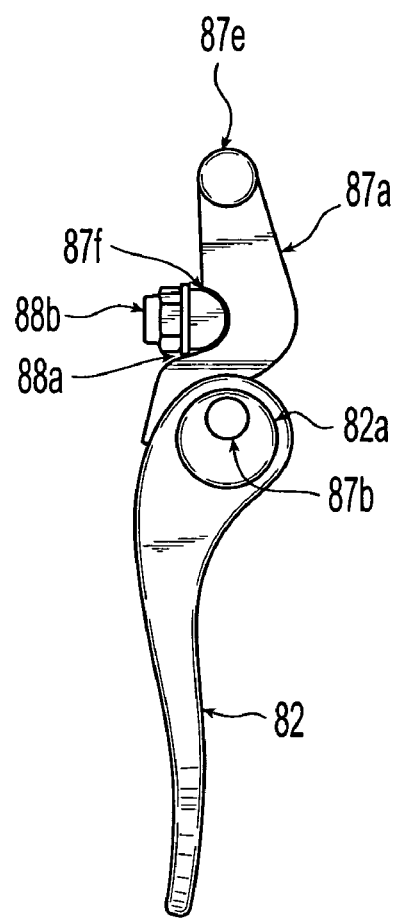
Figure 5S:
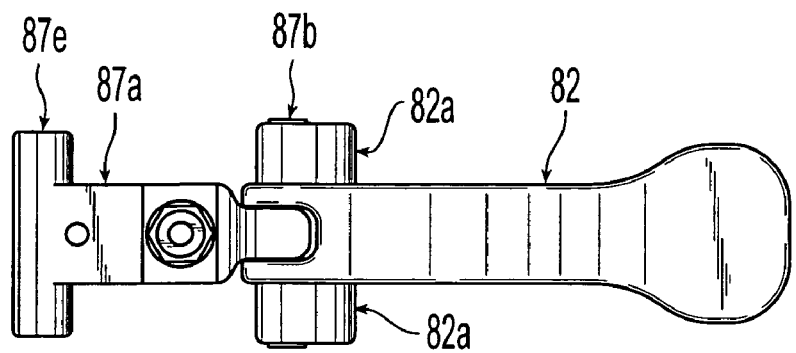
Figure 5T:
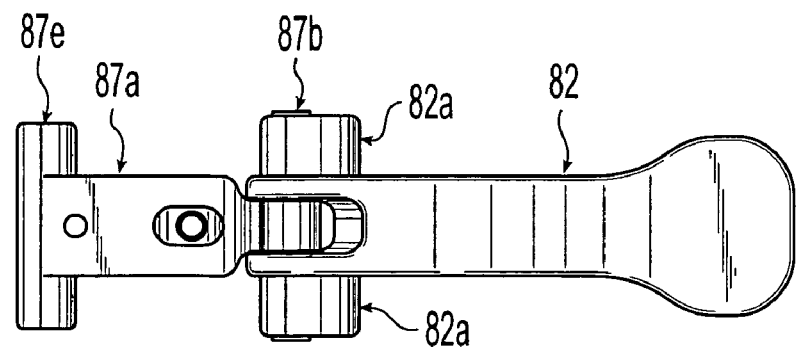
Figure 5U:
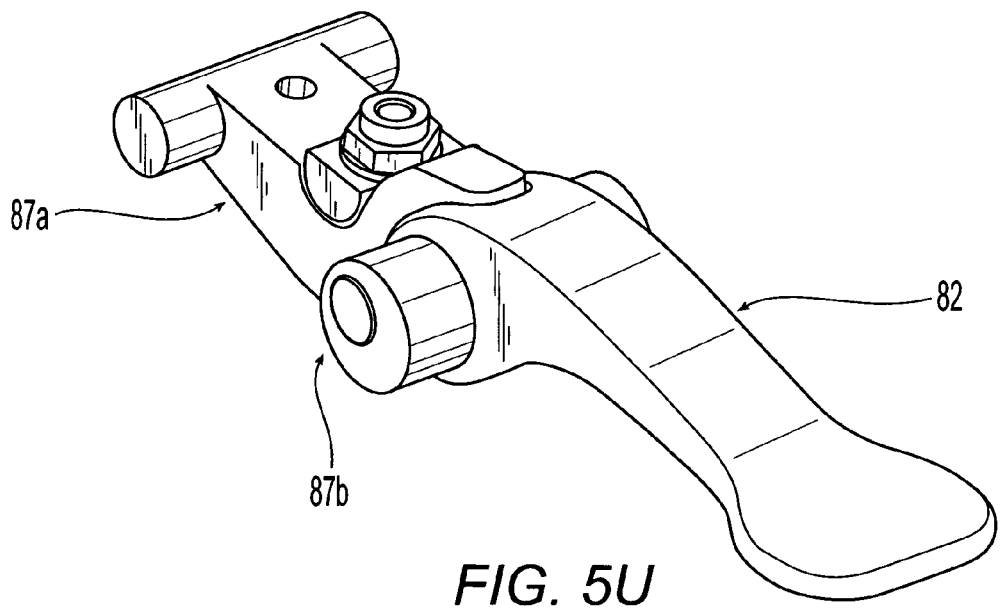
Figure 5V:
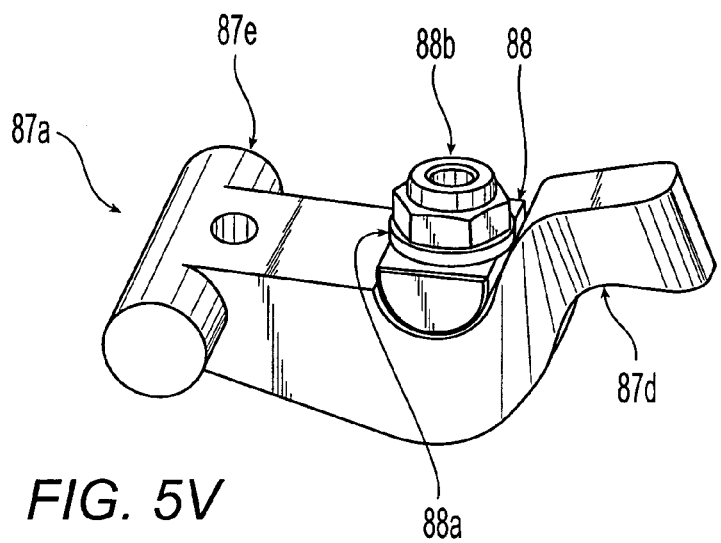
FIG. 5V shows a perspective view of the rocker arm of FIG. 5Q with a swage pivot associated therewith.
Figure 5W:
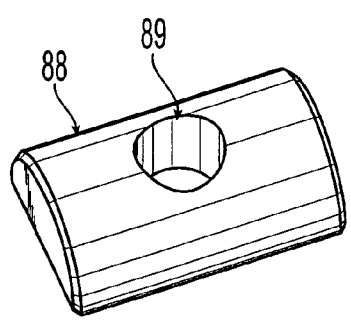
FIG. 5W shows a perspective view of the swage pivot of FIG. 5V.
Figure 6D:
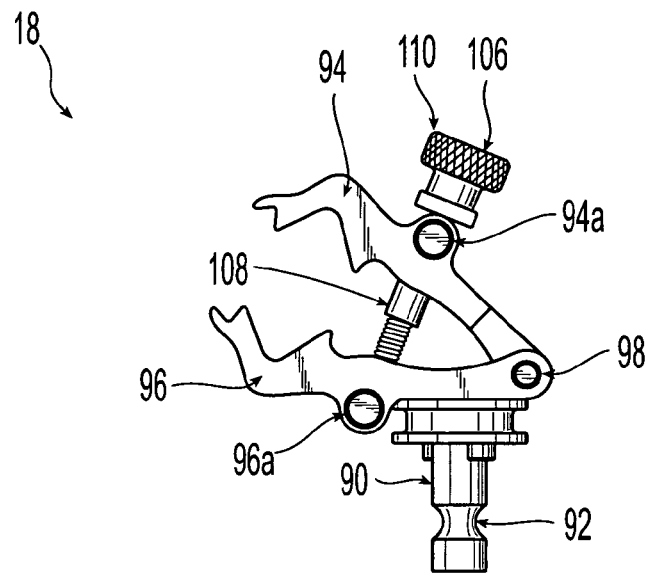
FIG. 6 shows the clamp end effector of FIG. 1, including (6A) a perspective view, (6B) a front view, (6C) a back view, (6D) a first side view, (6E) a second side view, (6F) a top view, and (6G) a bottom view.
Figure 6E:
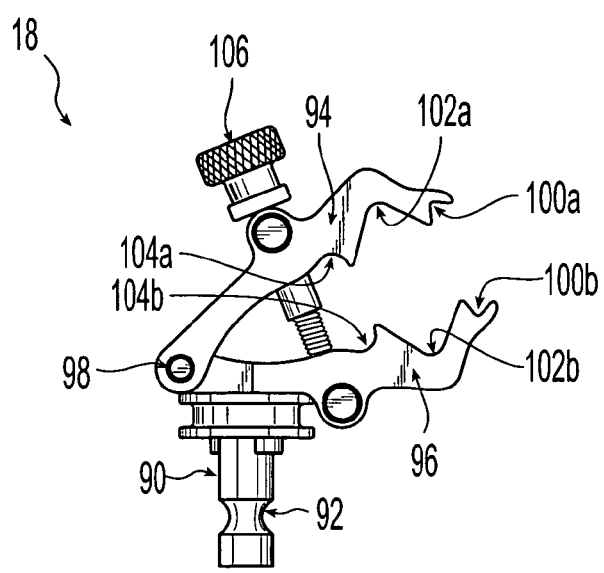
Figure 6F:
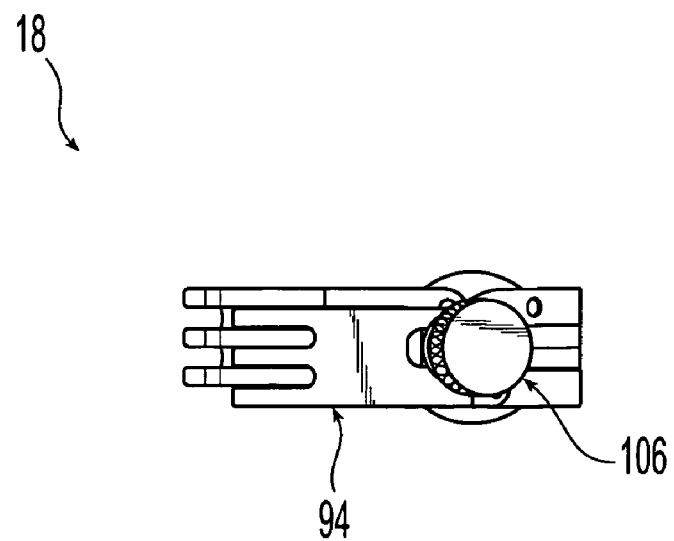
Figure 6G:
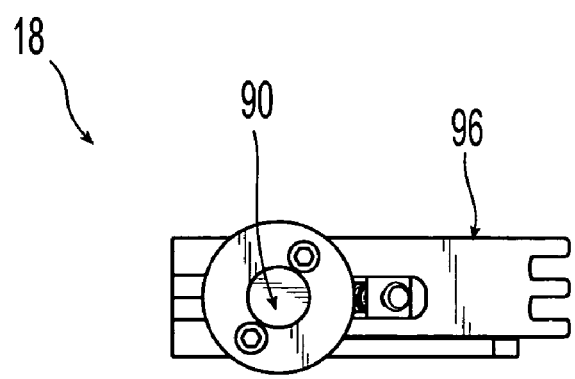

As shown in FIG. 5K, interface portion 84 may be operably associated with interface lock 83. Interface lock 83 includes a handle portion 83a and a cylindrical post 83b that is provided with an arcuate cutout 83c and a groove 83d. When post 83b is aligned with groove 85b in coupling portion 85a of interface portion 84, handle portion 83a may be rotated so that interface portion 84 is releasably coupled to free handle 62 and retained thereon. More specifically, the contour and sizing of groove 85b preferably matches the contour and sizing of arcuate cutout 83c, and thus when cutout 83c is aligned with groove 85b, as shown in FIG. 5K, interface lock 83 is in the unlocked position and thus interface portion 84 may be moved freely with respect thereto. When cutout 83c is not aligned with groove 85b, the cylindrical portion 83e of post 83b is received in groove 85b, and interface lock 83 is in the locked position and thus coupled to end effector receiving portion 81. In a preferred exemplary embodiment, cylindrical portion 83e may be frictionally fit in groove 85b to generally resist rotational movement of interface portion 84 with respect to interface lock 83. In addition, as shown in FIG. 5K, a set screw or locking screw 86 may be aligned with groove 83d, and also threadably associated with body portion 62a at a hole 62e to couple interface lock 83 to body portion 62a of free handle 62.

End effector receiving portion 81 is configured to receive and couple to an end effector such as a bracket or clamp, as shown for example in FIG. 1.

As shown for example in FIGS. 5Q to 5V, a cam arrangement 87 may be employed with lever 82. In particular, a rocker arm 87a is moveably associated with lever 82 via cylindrical dowel 87b which extends through lever 82. A cylindrical cam bushing 87c is mounted on dowel 87b and bears against arcuate surface 87d of rocker arm 87a, as shown for example in FIG. 5V. In addition, rocker arm 87a is provided with a cylindrical post 87e which bears against an arcuate surface 62b of body portion 62a. Thus, when lever 82 pivots about dowel 87b, cam action occurs such that the position of rocker arm 87a may move along central axis 62c of free handle 62.

Lever 82 includes a cylindrical portion 82a proximate an end thereof which may be slidably and rotatably associated with arcuate surface 62d of body portion 62a as shown for example in FIG. 5E.

Rocker arm 87a includes a cylindrical, arcuate recessed portion 87f in which bears against and seats a mating pivot or half-round bearing 88 with a through hole 89, which may further be provided with a flat washer 88a and internally-threaded lock nut 88b for use in coupling tensioning wire 58 to free handle 62. Tensioning wire 58 may be fitted on its end with a coupling (not shown) having a sleeve portion that is swaged or otherwise compressed thereon so that the wire 58 is securely coupled to the sleeve. In a preferred exemplary embodiment, the coupling preferably is formed of steel and is configured as a swage stud, while the lock nut is a nylock-type lock nut (a nut with a nylon insert to resist backing off). Integrally formed with the sleeve portion is an externally threaded end portion. Tensioning wire 58 may pass through hole 89 and washer 88a, and the coupling for wire 58 may be threadably associated with lock nut 88b so that wire 58 is retained. The initial pre-tension of wire 58 may be selected because the coupling for wire 58 may be threaded into lock nut 88b so that only some of the threads of lock nut 88b are associated therewith. Thus, when cam action occurs and rocker arm 87a moves with respect to central axis 62c, the orientation of tensioning wire 58 is changeable by swiveling of bearing 88 in recessed portion 87f. In a preferred exemplary embodiment, bearing 88 preferably is formed of a polymer.

The mechanism of operation of the cam action in free handle 62 is likewise applicable to second lever 68 of base handle 60. Moreover, the mechanism of attachment of wire 58 to free handle 62 is likewise applicable to base handle 60.

Curvilinear articulating arm assembly 14 thus may be coupled to tray 12 to permit a user to freely orient an object such as a medical device with respect to a patient disposed on tray 12 and releasably lock the position of the object with respect to the patient. Preferably, different levels of resistance to movement of arm 52 are provided by levers 68, 84 of handles 60, 62 respectively. For example, increased tensioning of wire 58 by free handle 62 may permit arm 52 to change from freely or loosely articulatable to more resilient motion, whereas increased tensioning of wire 58 by base handle 60 may permit arm 52 to be relatively stiff so that movement is resisted. Preferably, arm 52 is harder to rotate as a function of increasing size of ball 56a, 56b.

Curvilinear articulating arm assembly 14 preferably is formed of materials that may be used in the CT environment.

Referring now to FIG. 6, a clamp end effector 18 will be described. End effector 18 includes a coupling portion 90 in the form of a post with a groove 92 formed circumferentially therein. Coupling portion 90 preferably is configured to be received in portion 82 of free handle 62. The bayonet mounting provided by free handle 62 permits coupling portion 82 to be releasably engaged and locked to free handle 62. Clamp end effector 18 further includes jaws 94, 96 that are pivotably associated with each other about a pivot rod 98. When jaws 94, 96 are in a closed position with respect to one another, a variety of devices may be releasably held in regions defined by opposing portions 100a, 100b, opposing portions 102a, 102b, and/or opposing portions 104a, 104b as shown in FIG. 6E. Preferably, each of the opposing portions is generally V-shaped. Jaws 94, 96 each include a pivot rod 94a, 96a. Preferably, a screw 106 is associated with jaws 94, 96, with shaft 108 thereof extending through pivot rod 94a and threadably engaging a like-threaded hole in pivot rod 96a. Thus, by rotating head 110 of screw 106, jaws 94, 96 can be moved closer together or further apart from each other as the threaded portion of shaft 108 threads into or out of pivot rod 96a.

Figures 7A, 7B:
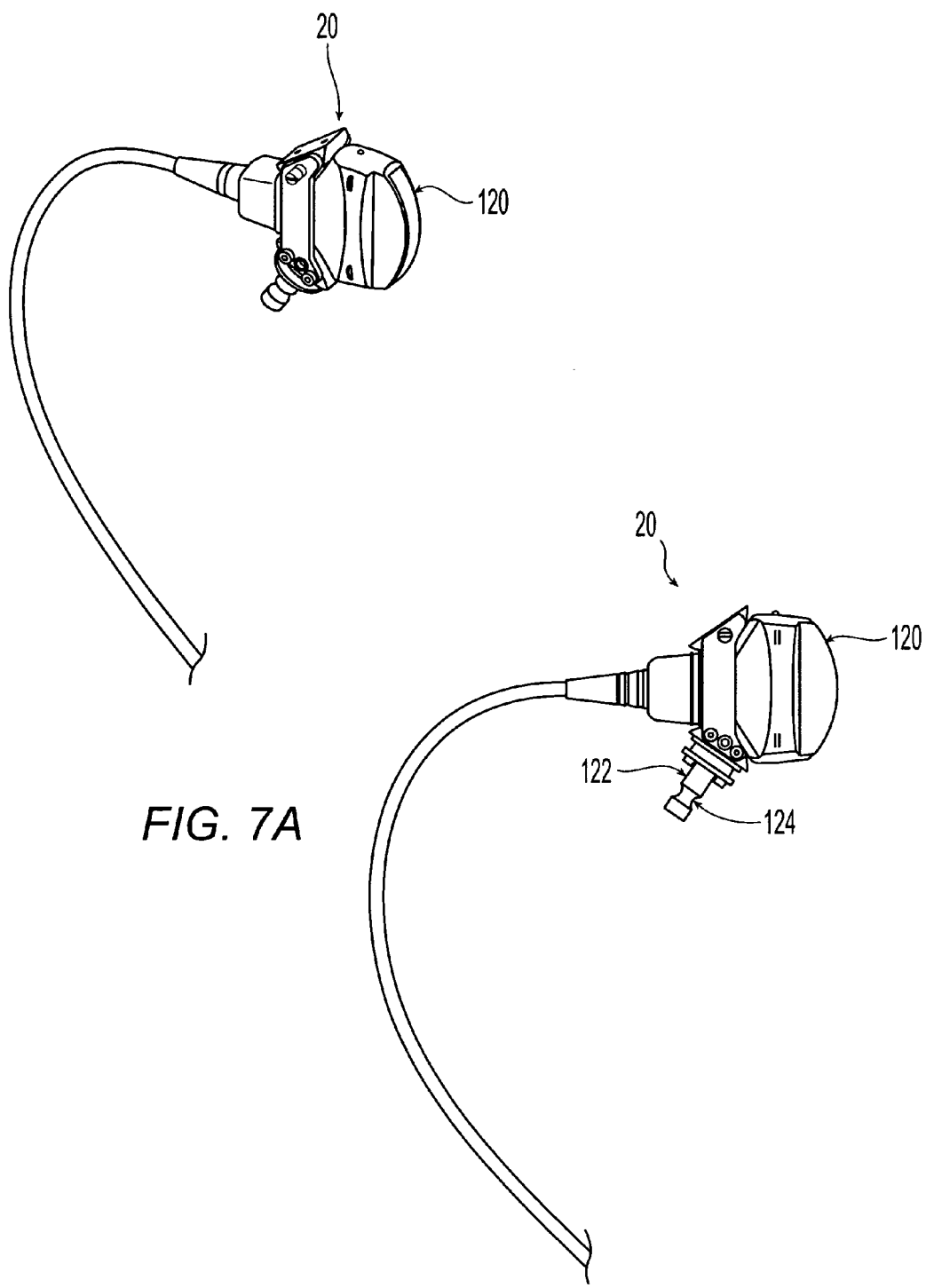
FIG. 7 shows the bracket end effector of FIG. 1, including (7A) a perspective view, and (7B) a side view.

An end effector 20 in the form of a self-centering abdominal probe bracket is shown in FIG. 7. Bracket 20 is configured and dimensioned to retain a device such as an ultrasound transducer 120 therein for use, for example, in connection with addressing respiratory gating as previously discussed. Also as previously discussed, end effector 20 includes a coupling portion 122 in the form of a post with a groove 124 formed circumferentially therein. Coupling portion 122 preferably is configured to be received in portion 82 of free handle 62. The bayonet mounting provided by free handle 62 permits coupling portion 122 to be releasably engaged and locked to free handle 62.

Additional components for use with tray 12 next will be described. As shown in FIG. 8, a rail assembly 26 is shown. Rail assembly 26 includes a coupling section 130 and a rail 132 spaced therefrom. In the preferred exemplary embodiment, coupling section 130 has a pair of couplings 134 that each have a threaded portion 136 that may be threadably received in a threaded insert (not shown) disposed in an attachment region 40 of tray 12. Preferably, couplings 134 are rotatable by actuation of a lever 138 so that a user may threadably engage each of couplings 134 to tray 12 (via a threaded insert therein) simply by actuation of lever 138. As shown in FIG. 1, when rail assembly 26 is couple to tray 12, rail 132 is raised above tray 12 and spaced from sides 36, 38 thereof. Rail 132 is thus demountably couplable to tray 12 in a desired location along sides 36, 38, and may be used to support equipment such as surgical devices that do not have end effectors readily couplable to attachment regions 40 of tray 12. For example, rail assembly may be used to couple various supports, retractors, arms boards, leg supports, and/or surgical guidance equipment to tray 12.

Figure 9:
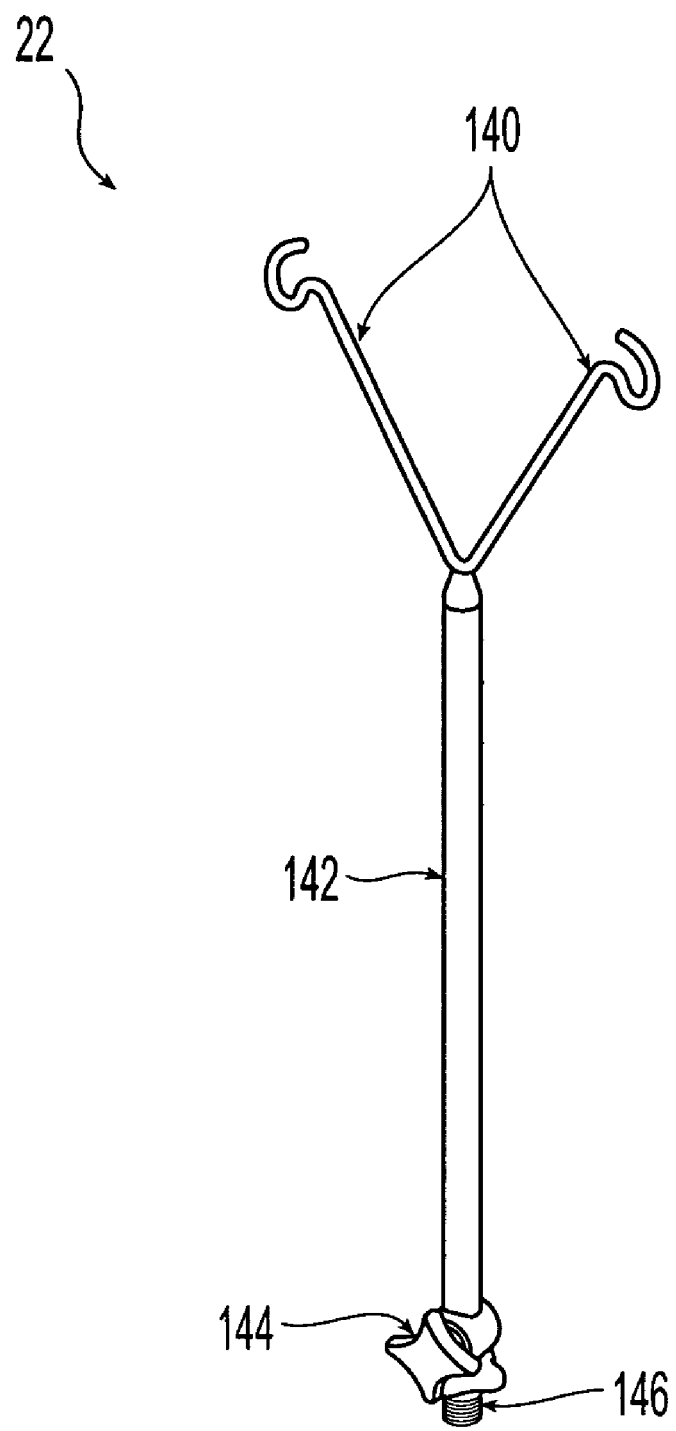
FIG. 9 shows a perspective view of the IV pole of FIG. 1.

An IV pole 22 is shown in FIG. 9. Pole 22 includes hooks 140, telescoping pole 142, screw lock 144 for locking pole 142 at a desired extension thereof, and a coupling 146 having a threaded portion that may be threadably received in a threaded insert (not shown) disposed in an attachment region 40 of tray 12.

An arm board 24 is shown in FIG. 10. Arm board 24 includes a board portion 150 and couplings 152. Couplings 152 each have a threaded portion that may be threadably received in a threaded insert (not shown) disposed in an attachment region 40 of tray 12 to demountably attach arm board 24 thereto. At least one cutout 154 also may be provided for receiving an object therethrough or alternatively for making arm board 24 lighter. In a preferred exemplary embodiment, arm board 24 includes sides 156, 158 that are disposed transverse to one another so that a first end 160 of arm board 24 is wider than a second end 162 thereof. Arm board 24 for example may be formed of aluminum.

A lift beam assembly 170 is shown in FIG. 11. Lift beam assembly 170 may be used as a pair with one mounted on each side of the tray to removably couple support system 10 to the frame of an OR table. For example, in the preferred exemplary embodiment three couplings 172a, 172b, 172c may be provided, with each having a threaded portion that may be threadably received in a threaded insert (not shown) disposed in an attachment region 40 of tray 12 to demountably attach assembly 170 thereto. Preferably, coupling 172c may then be releasably coupled to the central platform of an electrohydraulically operated operating room table. Region 174 of the beam reacts against the underside of this central platform as the hydraulic lift mechanism begins to lift the tray. All movements present in the operating mechanism of the OR table may then be used to position or orient the tray.

Figure 12:
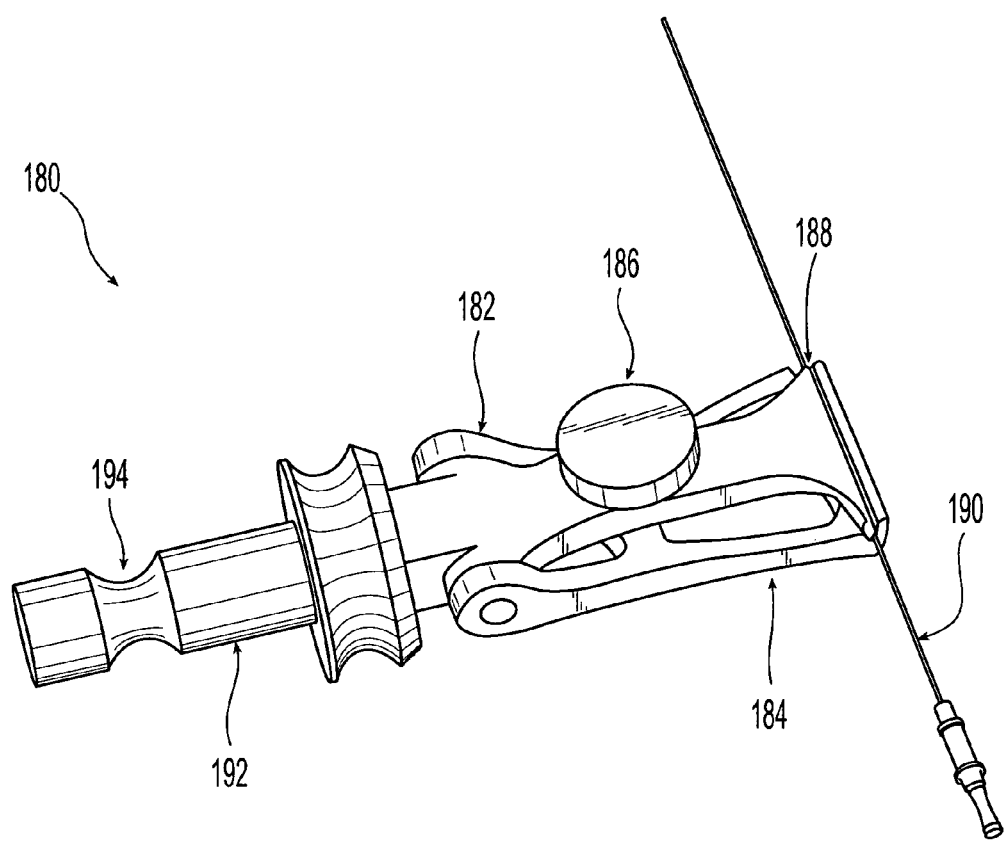
FIG. 12 is a perspective view of another end effector according to the present invention.

Finally, yet another end effector for use in fine needles probes, or catheters is shown in FIG. 12. As can be seen, a pair of clamping plates 182, 184 are connected by a central screw 186. Clamping plates 182, 184 are provided with a groove opposing a rounded edge 188 proximate free ends thereof, and an instrument 190 may be grasped within the grooves. As discussed with other embodiments, end effector 180 includes a coupling portion 192 in the form of a post with a groove 194 formed circumferentially therein. Coupling portion 192 preferably is configured to be received in portion 82 of free handle 62. The bayonet mounting provided by free handle 62 permits coupling portion 192 to be releasably engaged and locked to free handle 62.

Figure 13:
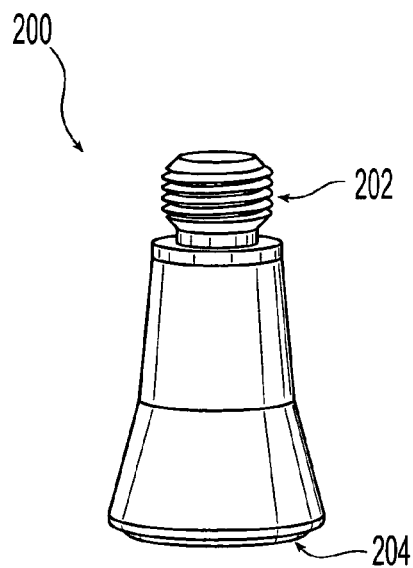
FIG. 13 shows a perspective view of a stabilizing post for use with the support system according to the present invention.

As described previously, tray 12 may be provided with a central arcuate portion 42. If tray 12 is to be placed on a rigid or semi-rigid flat surface, for example a flat ultrasound table, a patient in tray 12 may not be stable because of the tendency of central arcuate portion 42 to swivel about the contact region between portion 42 and the flat surface. In order to stabilize tray 12 on such a surface, as shown in FIG. 13, stabilizing posts 200 or "feet" may be provided. In an exemplary preferred embodiment, four posts 200 may be provided to stabilize tray 12, one disposed proximate each of the four corners of tray 12. Preferably, posts 200 are sized to provide sufficient support below outer ledge portions 44 to accommodate the portion of the vertical height h from the lowermost surface of tray 12 to lower surface 44b of outer ledge portion 44. Advantageously, posts 200 include a threaded shaft 202 and a friction tip 204 disposed proximate one end of the post. Tip 204 preferably is formed of a material such as rubber that resist sliding on surfaces. Thus, threaded holes may be provided along lower surface 44b to threadably receive the posts 200. In addition, to accommodate variations in the surface on which tray 12 rests as well as to address situations in which such a surface may not be "level," one or more of the posts may be only partially threaded in its respective hole so that tray 12 may be stabilized, and potentially leveled, by providing varying post heights extending from lower surface 44*b*.

Figure 14:
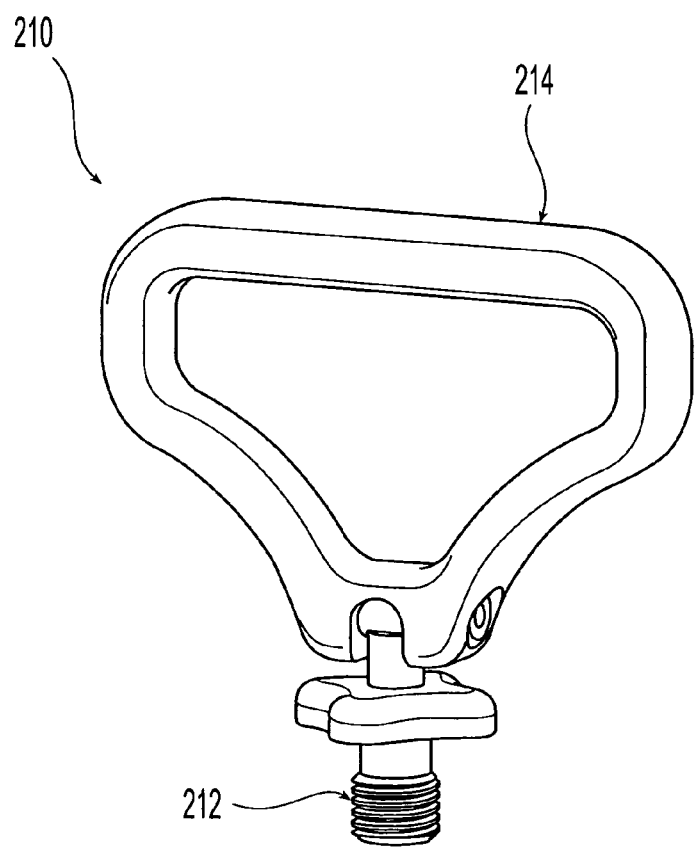
FIG. 14 shows a perspective view of a handle for use with the support system according to the present invention.

Turning to FIG. 14, a handle 210 is shown for attachment to tray 12. Once coupled to tray 12, for example by threadable association of coupling 212 with an attachment region 40, handle 210 may be held at hand grip portion 214 to facilitate movement of tray 12 particularly when a patient is supported thereon. In an exemplary preferred embodiment, at least two handles 210 are coupled to tray 12, and in one embodiment four handles 210 are provided.

Some embodiments of support system 10 may provide one or more of the following: assist in stabilization and control of guidance devices and accessory instrumentation during image guided procedures; improved patient positioning and stabilization during imaging and image guided procedures; enabling of the use of ultrasound for respiratory gating during abdominal or thoracic image guided procedures (e.g., through the use of an arm assembly 14 for holding an ultrasound transducer in a position against the abdominal or chest wall to view the position of the diaphragm in real time during imaging in the CT or MR gantry); generally improved accuracy of targeting and placement of instruments during image guided procedures by holding instruments in a fixed relationship to the patient as the patient is moved for imaging purposes. In addition, some of the embodiment of support system 10 may be used in one or more of the following applications: integrated general laparoscopic surgical procedures with CT and MR image guidance; integrated computer assisted surgical tracking and navigation systems and robotic surgical devices with the CT and MR imaging systems.

One method of use of the of the present invention may for example include: placing a patient on the tray such as after locating and fixing the tray onto the pre-existing table or tray of a scanner (in the tray-on-tray model); positioning the patient in an optimal position on the tray and securing the patient in that position using a shape conforming mattress and accessory extremity support devices that may be attached to the tray as required; obtaining the appropriate images using the scanner with the patient in this optimal position; mounting lockable positioning arm(s) at desired site(s) alongside the patient by considering the instruments required, the position of the target site and the position of the operating physician; preparing and draping the surgical field; choosing an appropriate sterile end effector(s) for the arms and attaching them to the arms in conjunction with a sterile sleeve type drape to cover the arms to complete the protection of the sterile field; indexing one or more of the arms with the imaging plane of the scanner and registering the instrument that it holds with an image if required; capturing desired equipment or devices in the end effectors and positioning the equipment or devices as desired; re-imaging and re-positioning the arms/equipment based on new images or as otherwise desired during the procedure.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. For example, attachments regions 40 may comprise other releasably lockable constructions to accommodate, for example, quick locking of components to tray 12, frictional locking, magnetic locking, or other modes of securement. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A system for supporting a patient during computed axial tomography imaging comprising:
   a movable platform formed of a radiolucent material;
   a discrete attachment region in the platform;
   a curvilinear articulating arm coupled to the platform at the discrete attachment region, the curvilinear articulating arm comprising:
     a plurality of balls and sleeves disposed on a tensioning wire;
     a first pivotable lever disposed proximate a first end of the curvilinear articulating arm and operably associated with a coupling for releasably securing the curvilinear articulating arm to the platform at the discrete attachment region;
     a second pivotable lever disposed proximate the first end of the curvilinear articulating arm and operably associated with the tensioning wire for adjusting tension thereof to vary flexibility of the curvilinear articulating arm; and
     a third pivotable lever disposed proximate a second end of the curvilinear articulating arm and operably associated with a rocker arm and the tensioning wire for adjusting tension thereof to vary flexibility of the curvilinear articulating arm;
   wherein the second and third levers permit different levels of resistance to movement of the curvilinear articulating arm.

2. The system of claim 1, further comprising an end effector demountably attached to the articulating arm.

3. The system of claim 2, wherein the end effector comprises a clamp.

4. The system of claim 2, wherein the end effector comprises a bracket.

5. The system of claim 2, wherein the end effector comprises a linear instrument guide.

6. The system of claim 2, further comprising an ultrasound transducer supported by the end effector.

7. The system of claim 1, wherein the platform comprises a plurality of openings forming hold regions disposed proximate a cranial end and a caudal end thereof.

8. The system of claim 1, wherein a plurality of discrete attachment regions are provided in spaced arrangement proximate the perimeter of the platform.

9. The system of claim 1, wherein the platform comprises a central arcuate portion disposed between a pair of ledge portions.

10. The system of claim 1, further comprising a cushion.

11. The system of claim 1, wherein the at least one discrete attachment region comprises a threaded insert.

12. The system of claim 1, wherein the curvilinear articulating arm comprises a plurality of ball and socket connections.

* * * * *